United States Patent
Salbeck et al.

(10) Patent No.: US 6,509,110 B1
(45) Date of Patent: Jan. 21, 2003

(54) TRIPTYCENE DERIVATIVES AND THEIR USE FOR OPTO-ELECTRONICS APPLICATIONS, IN PARTICULAR AS ELECTROLUMINESCENT MATERIALS

(75) Inventors: Josef Salbeck, Kaufungen (DE); Heinrich Becker, Glashütten (DE); Willi Kreuder, Mainz (DE); Karl Heinz Weinfurtner, Berlin (DE)

(73) Assignee: Axiva GmbH, Frankfurt (DE)

( * ) Notice: Subject to any disclaimer, the term of this patent is extended or adjusted under 35 U.S.C. 154(b) by 0 days.

(21) Appl. No.: 09/529,048

(22) PCT Filed: Sep. 8, 1998

(86) PCT No.: PCT/EP98/05686

§ 371 (c)(1),
(2), (4) Date: Aug. 4, 2000

(87) PCT Pub. No.: WO99/19419

PCT Pub. Date: Apr. 22, 1999

(30) Foreign Application Priority Data

Oct. 10, 1997 (DE) .......................... 197 44 792

(51) Int. Cl.$^7$ .............................. H05B 33/14
(52) U.S. Cl. ...................... 428/690; 428/917; 428/704; 313/504; 313/506; 252/301.35; 257/40; 257/103
(58) Field of Search ................ 428/690, 917, 428/704; 313/504, 506; 252/301.35; 257/40, 103; 556/64, 406

(56) References Cited

U.S. PATENT DOCUMENTS 4,539,507 A 9/1985 Van Slyke et al. .......... 313/504

OTHER PUBLICATIONS

Wasielewski, M.R., et al, *J. Am. Chem. Soc. 107*: 5562–3, XP–002092033 (1985). No Month.
Wasielewski, M.R., et al, *Tetrahedron 45*:4785–4805, XP–002092034 (1989). No Month.
Abstract of published Japanese appln. JP–63/117013 (Chisso Corp) (May 21, 1988).
Abstract of published Japanese appln. JP–05/158092 (Hitachi Ltd.) (Jun. 25, 1993).
Abstract of published Japanese appln. JP–63/115832 (Chisso Corp.) (May 20, 1988).
Wilhard, P., abstract of published German appln. DE–41 21 138 (Hoechst AG) (Mar. 7, 1993).

*Primary Examiner*—Deborah Jones
*Assistant Examiner*—Ling Xu
(74) *Attorney, Agent, or Firm*—Connolly Bove Lodge & Hutz LLP

(57) ABSTRACT

Triptycene derivatives, and their use for opto-electronic applications, in particular as electroluminescent materials Triptycene devices of the formula (I)

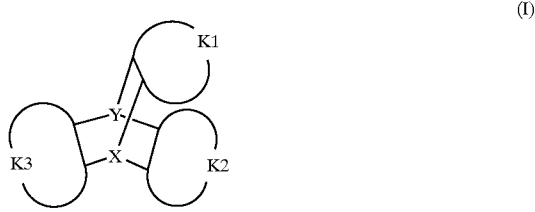

(I)

where the symbols in the formula have the following meanings:

$K^1$, $K^2$ and $K^3$ are identical or different and are mono- or polycyclic systems, which may, if desired, contain heteroatoms, preferably N, S and/or O, and;

X and Y are identical or different and are $CR^1$, N, P, As or $SiR^2$;

$R^1$ are identical or different and are H, halogen, pseudohalogen or a hydrocarbon radical having 1 to 30 carbon atoms, which may also, if desired, contain heteroatoms, preferably —O—, —N— and/or —S—;

$R^2$ are identical or different and are a hydrocarbon radical having 1 to 30 carbon atoms, which may also, if desired, contain heteroatoms, preferably —O—, —N— and/or —S—, are suitable for use in electroluminescent devices.

8 Claims, No Drawings

TRIPTYCENE DERIVATIVES AND THEIR USE FOR OPTO-ELECTRONICS APPLICATIONS, IN PARTICULAR AS ELECTROLUMINESCENT MATERIALS

DESCRIPTION

Triptycene derivatives, and their use for optoelectronic applications, in particular as electroluminescent materials There is a considerable industrial demand for large-area solid-state light sources for a number of applications, predominantly in the area of display elements, display screen technology and illumination technology. The requirements made of these light sources can currently not be met entirely satisfactorily by any of the existing technologies.

As an alternative to conventional display elements, such as incandescent lamps, gas-discharge lamps and non-self-illuminating liquid-crystal display elements, electroluminescent (EL) materials and devices, such as light-emitting diodes (LEDs), have already been known for some time.

Electroluminescent materials are substances which are capable of emitting light on application of an electric field. The physical model for describing this effect is based on the recombination of electrons and electron holes, with emission of light. In light-emitting diodes, the charge carriers are injected into the electroluminescent material via the negative electrode or positive electrode. Electroluminescent devices contain a luminescent material as light-emitting layer. Electroluminescent materials and devices have been described in general terms, for example, in Ullmann's Encyclopedia of Industrial Chemistry, Vol. A9, 5th Ed., VCH Verlag, 1987 and the references cited therein. Besides inorganic substances, such as ZnS/Mn or GaAs, organic compounds have also been disclosed as EL materials.

A description of EL devices containing low-molecular-weight organic EL materials is given, for example, in U.S. Pat. No. 4,539,507.

Although good results have been achieved using such materials, the property profile of such compounds leaves plenty of room for improvement.

Since, in addition, the development of electroluminescent materials can in no way be regarded as complete, the manufacturers of illumination and display devices continue to be interested in a very wide variety of electroluminescent materials for such devices.

One of the reasons for this is that only the interaction of the electroluminescent material with the other components of the devices allows conclusions to be drawn on the suitability of the electroluminescent material too.

The object of the present invention was therefore to provide novel electroluminescent materials which, on use in illumination or display devices, are suitable for improving the property profile of these devices.

Surprisingly, it has now been found that certain derivatives of triptycene are particularly suitable for use as electroluminescent materials.

The invention therefore relates to the use of a triptycene derivative of the formula (I) in electroluminescent devices,

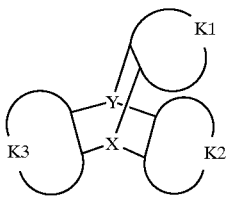

(I)

where the symbols in the formula have the following meanings:

$K^1$, $K^2$ and $K^3$ are identical or different and are mono- or polycyclic systems, which may, if desired, contain heteroatoms, preferably N, S and/or O, and are substituted or unsubstituted;

X and Y are identical or different and are $CR^1$, N, P, As or $SiR^2$;

$R^1$ are identical or different and are H, halogen, pseudohalogen or a hydrocarbon radical having 1 to 30 carbon atoms, which may also, if desired, contain heteroatoms, preferably —O—, —N— and/or —S—;

$R^2$ are identical or different and are a hydrocarbon radical having 1 to 30 carbon atoms, which may also, if desired, contain heteroatoms, preferably —O—, —N— and/or —S—.

Compounds of the formula (I) are distinguished by adequate to good solubility in common organic solvents, good film-forming properties and a reduced tendency toward crystallization. The production of electroluminescent devices is thus simplified and their life extended. The emission properties of the compounds employed in accordance with the invention can be adjusted over the entire range of the visible spectrum through the choice of suitable substituents. In addition, the covalently bonded arrangement of the various parts of the triptycene compound allows a molecular structure such that certain properties can be set independently in different parts of the molecule. Thus, one part can have, for example, charge-transport or charge-injection properties, while the other has light-emitting properties.

At least one of the systems $K^{1-3}$ is preferably a fluorophore. For the purposes of the invention, a fluorophore is an atomic group which imparts fluorescence on the triptycene derivative, for example an extended aromatic system.

It is furthermore preferred for all three systems $K^{1-3}$ to be conjugated. Preferred, substituted or unsubstituted and/or bicyclic or polycyclic conjugated systems are:

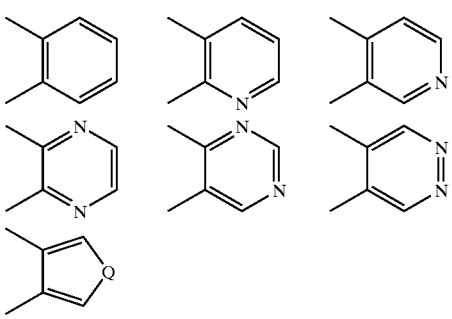

where Q=S, O or $NR^2$.

Particularly preferred compounds of the general formula (I) are triptycene derivatives of the formula (II) and of the formula (III)

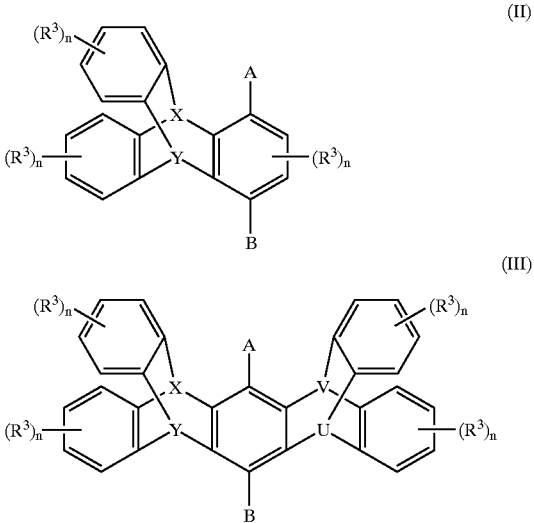

(II)

(III)

where the symbols and indices have the following meanings:
X, Y, U and V are identical or different and are $CR^1$, N, P, As or $SiR^2$;

$R^1$ are identical or different and are H, halogen, pseudohalogen or a hydrocarbon radical having 1 to 30 carbon atoms, which may also, if desired, contain heteroatoms, preferably —O—, —N— and/or —S—;

$R^2$ are identical or different and are a hydrocarbon radical having 1 to 30 carbon atoms, which may also, if desired, contain heteroatoms, preferably —O—, —N— and/or —S—.

$R^3$ are identical or different and are, F, Cl, Br, I, CN, $NO_2$, a branched or unbranched alkyl group having 1 to 22 carbon atoms, where one or more —$CH_2$— groups may be replaced by —O—, —S—, —$SO_3$—, —O—CO—, —CO—O—, aryl or heteroaryl (in each case having 4 to 10 carbon atoms), with the proviso that two oxygen atoms cannot be bonded directly to one another, and where one, more or all H atoms may be replaced by F, and where two substituents $R^2$ on the same ring may be linked to one another to form a ring or a further fused ring system or may also be hydrogenated, if desired partially, and may carry substituents, preferably of the type $R^1$, with the proviso that the number of substituents is not greater than the total number of carbon atoms;

n are identical or different and are 0, 1, 2, 3, 4 or 5;

A and B are identical or different and are groups of the formula

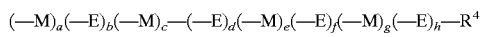

where the symbols and indices have the following meanings:
M are identical or different and are —$CR^5$=$CR^6$—, —C≡C—, —$CR^7$=N— or —N=$CR^7$—;

E are identical or different and are pyrazine-2,5-diyl, pyridazine-3,6-diyl, pyridine-2,5-diyl, pyrimidine-2,5-diyl, 1,3,4-thiadiazole-2,5-diyl, 1,3-thiazole-2,4-diyl, 1,3-thiazole-2,5-diyl, thiophene-2,4-diyl, thiophene-2,5-diyl, naphthalene-2,6-diyl, naphthalene-1,4-diyl or naphthalene-1,5-diyl, in which one or two CH groups may be replaced by N, 1,3-oxazole-2,4-diyl, 1,3-oxazole-2,5-diyl, 1,3,4-oxadiazole-2,5-diyl, 4,4'-bi-phenylene, anthracenediyl, carbazolediyl, benzoxazolediyl, indene-2,5-diyl or indene-2,6-diyl, where one or more H atoms in the ring systems may be substituted by radicals $R^8$;

$R^4$, $R^5$, $R^6$ and $R^7$ are identical or different and are
a) hydrogen, —F, —Cl, —$CF_3$, —CN or $NR^9R^{10}$,
b) a straight-chain or branched alkyl radical (with or without an asymmetrical carbon atom) having 1 to 20 carbon atoms, where
b1) one or more non-adjacent and non-terminal $CH_2$ groups may be replaced by —O—, —S—, —CO—, —CO—O—, —O—CO—, —O—CO—O— or —Si($CH_3$)$_2$—, and/or
b2) one or more $CH_2$ groups may be replaced by —CH=CH—, —C≡C—, cyclopropane-1,2-diyl, 1,4-phenylene, 1,4-cyclohexylene or 1,3-cyclopentylene, and/or
b3) one or more H atoms may be replaced by F, CN and/or Cl;

$R^8$ are identical or different and are
a) —F, —Cl, —$CF_3$, —CN or $NO_2$
b) a straight-chain or branched alkyl radical (with or without an asymmetrical carbon atom) having 1 to 20 carbon atoms, where
b1) one or more non-adjacent and non-terminal $CH_2$ groups may be replaced by —O—, —S—, —CO—, —CO—O—, —O—CO—, —O—CO—O—, —NH—, N($C_1$-$C_{10}$-alkyl), —N-phenyl-, —N-tolyl-, —N($C_2H_5$—$OCH_3$)— or —Si($CH_3$)$_2$—, and/or
b2) one or more $CH_2$ groups may be replaced by —CH=CH—, —C≡C—, 1,4-phenylene, and/or
b3) one or more H atoms may be replaced by F, CN and/or Cl;

$R^9$ and $R^{10}$ are identical or different and are
a) hydrogen,
b) a straight-chain or branched alkyl radical (with or without an asymmetrical carbon atom) having 1 to 20 carbon atoms, where
b1) one or more $CH_2$ groups which are not adjacent to one another or to the nitrogen may be replaced by —O—, —S—, —CO—, —CO—O—, —O—CO—, —O—CO—O— or —Si($CH_3$)$_2$—, and/or
b2) one or more $CH_2$ groups may be replaced by —CH=CH—, —C≡C—, cyclopropane-1,2-diyl, 1,4-phenylene, 1,4-cyclohexylene or 1,3-cyclopentylene, and/or
b3) one or more H atoms may be replaced by F, CN and/or Cl and
b4) $R^8$ and $R^9$ together may also form a ring;

a, b, c, d, e, f, g and h, independently of one another, are 0 or 1. The sum of the indices is preferably at least 1, particularly preferably at least 2. The sum b+d+f+h is particularly preferably ≧1, very particularly preferably ≧2.

Particularly preferred compounds of the formula (I) are the compounds of the formulae (IV), (V) and (VI),
(IV)
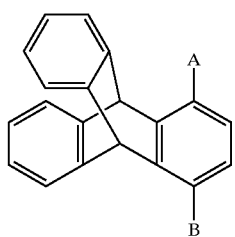
(V)
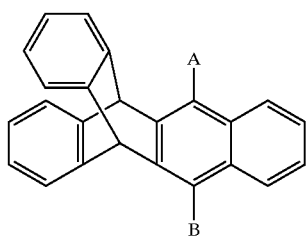
(VI)
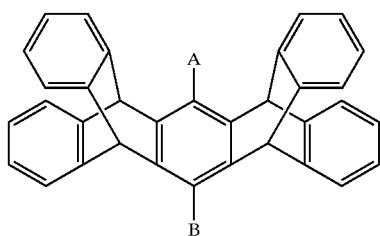
where the groups A and B are as defined above.
Particularly preferred compounds of the formulae (IV), (V) and (VI) are those of the formulae (IV), (V) and (VI) a-i:
(IVa)
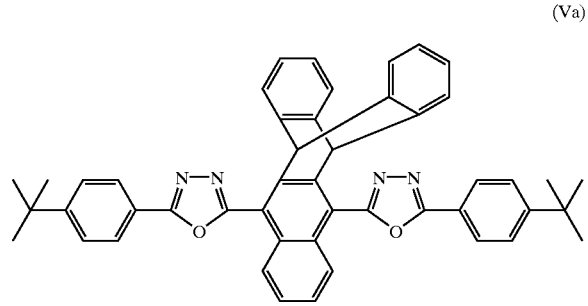
(Va)
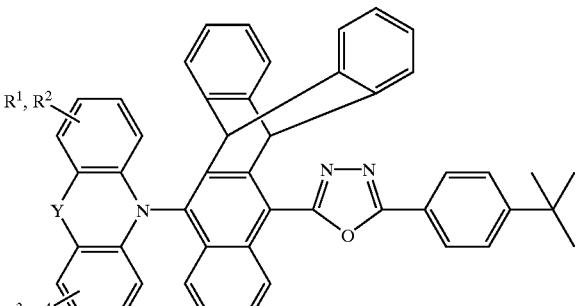
(VIa)
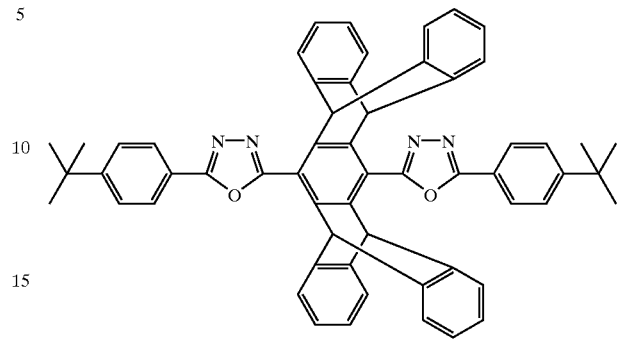
(IVb)
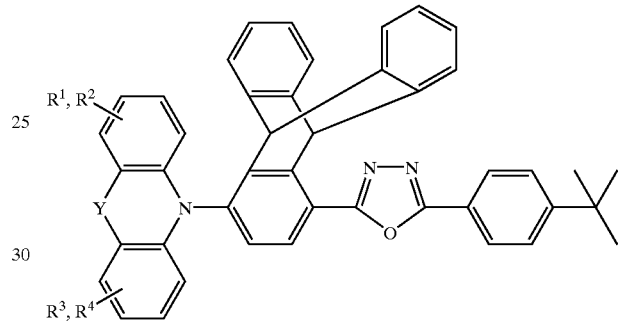
(IVc)
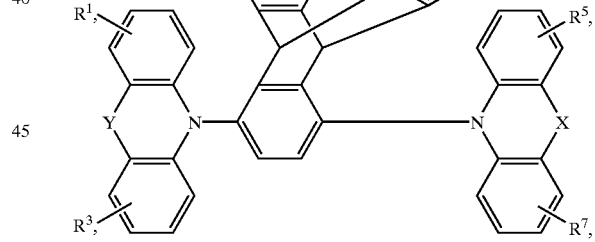
(Vb)

(Vc)
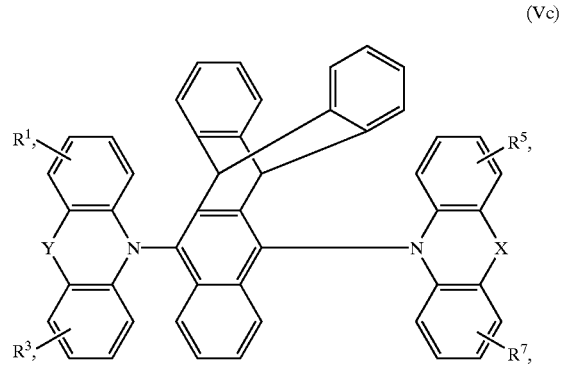
(VIb)
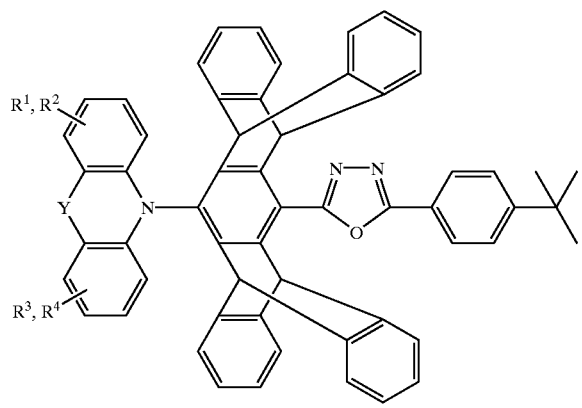
(VIc)
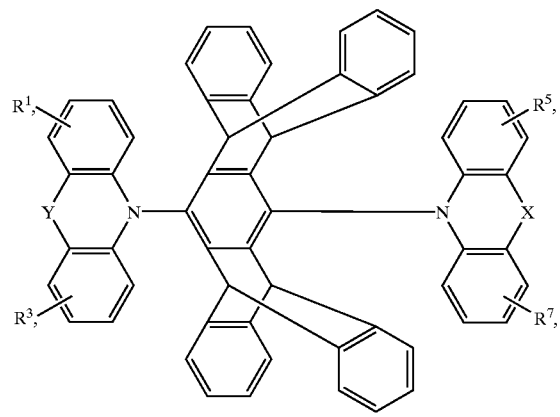
(IVd)
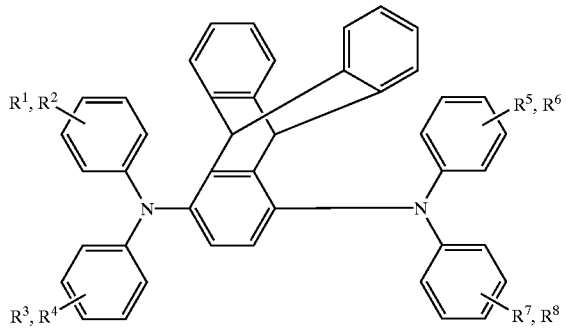
(IVe)
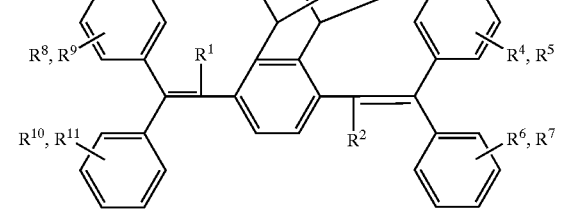
(Vd)
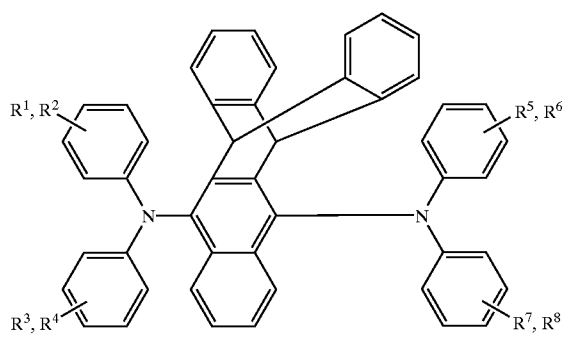
(Ve)
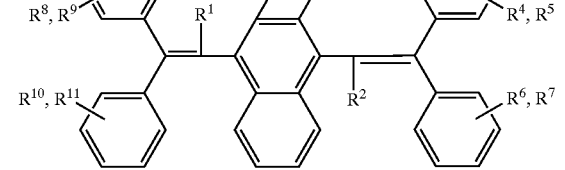
(VId)
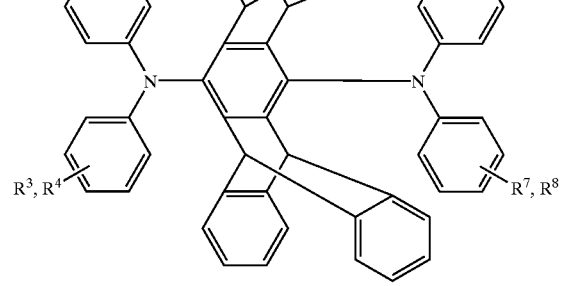

(VIe)
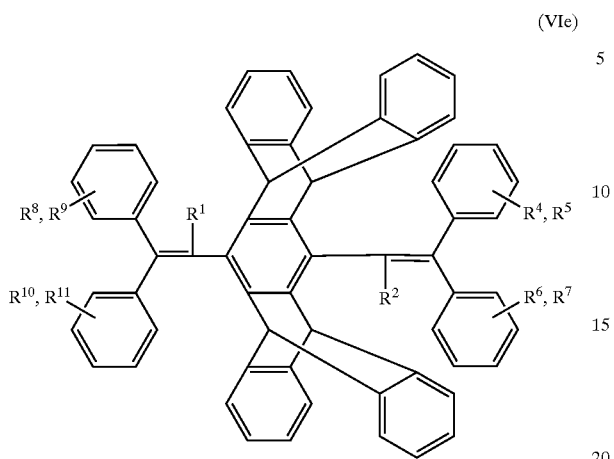
(IVf)
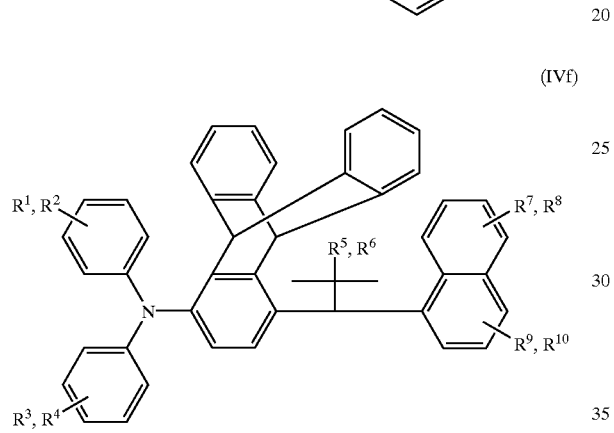
(IVg)
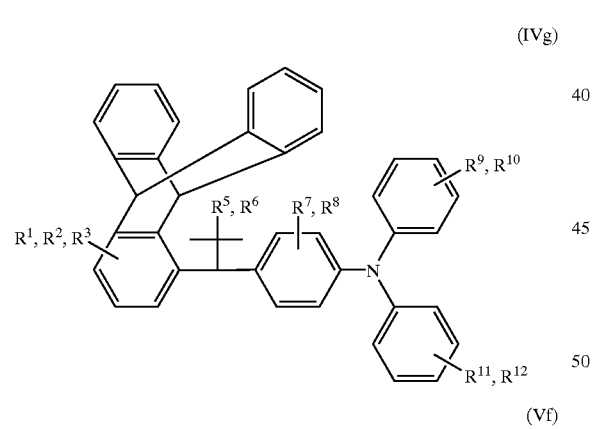
(Vf)
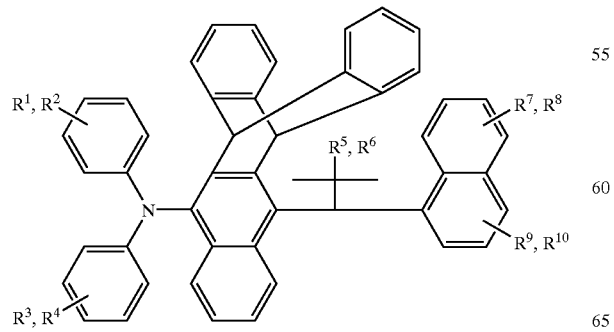
(Vg)
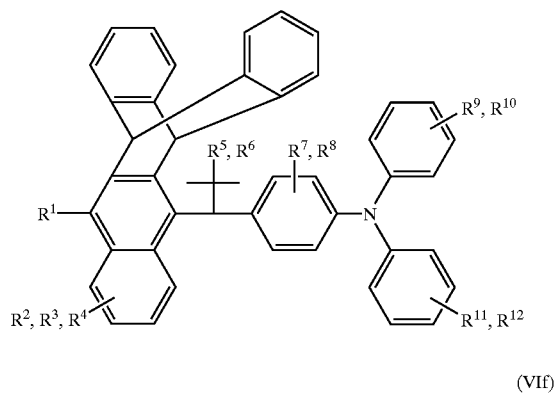
(VIf)
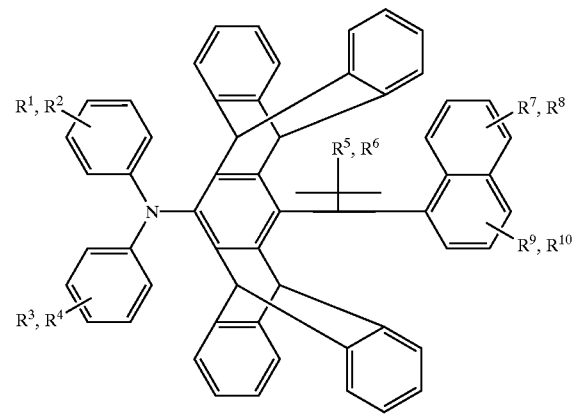
(VIg)
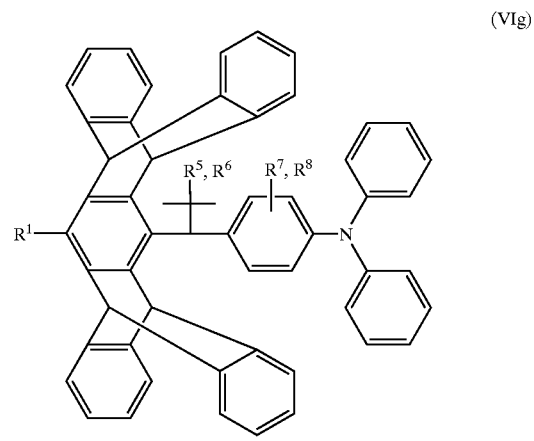
(IVh)
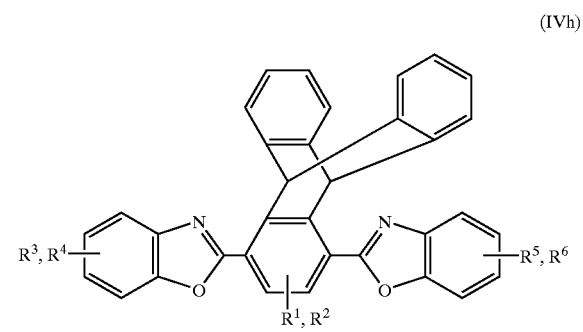

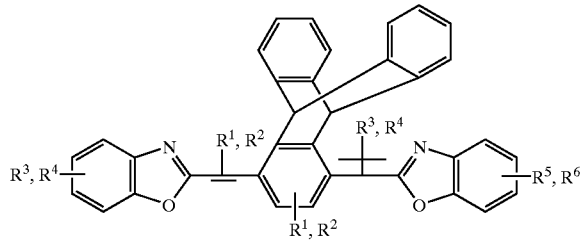
(IVi)

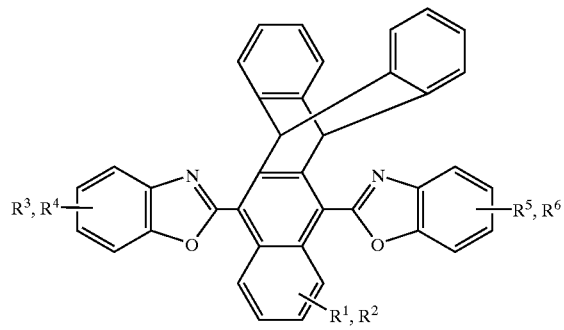
(Vh)

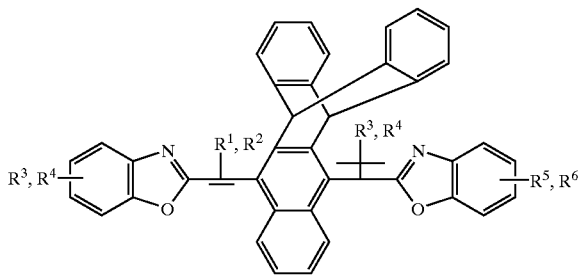
(Vi)

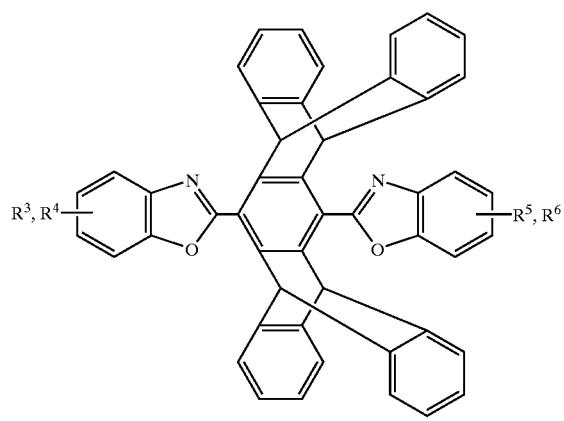
(VIh)

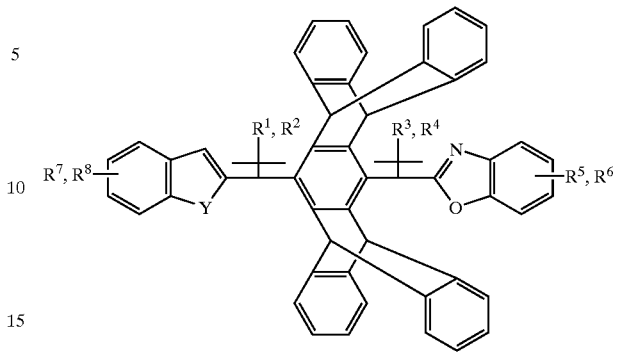
(VIi)

where the radicals $R^{1-11}$ are as defined for $R^3$ in the formulae (II) and (III), and Y is O, S, $NR^{11}$ or $CR^{10}R^{11}$.

The invention also relates to triptycene derivatives in which at least one of the groups $K^{1-3}$ is a fluorophore. The invention likewise relates to triptycene derivatives of the formulae (II) and (III) in which the sum of the indices a-h is at least 1, preferably at least 2.

The triptycene compounds according to the invention are prepared by methods known per se from the literature, as described in the standard works of organic synthesis, for example Houben-Weyl, Methoden der Organischen Chemie [Methods of Organic Chemistry], Georg-Thieme-Verlag, Stuttgart, and in the corresponding volumes of the series "The Chemistry of Heterocyclic Compounds" by A. Weissberger and E. C. Taylor (editors).

The preparation is carried out under reaction conditions which are known and suitable for said reactions. Use can also be made here of variants which are known per se, but are not mentioned here in greater detail.

Compounds of the formula (II) can be synthesized, for example, starting from substituted triptycene or a heterotriptycene parent compound, which is in turn accessible by various synthetic routes. The following may be mentioned by way of example, but not in a restrictive manner:

1. Synthesis from substituted anthracene (or substituted acridine or substituted phenazine) and dehydroaromatic compounds, for example starting from
   a) substituted o-fluorobromobenzenes with reactive metals, such as, for example, magnesium, for example analogously to G. Wittig, Org. Synth. IV 1963, 964;
   b) substituted o-dihalobenzenes and butyllithium with elimination of metal halide, for example analogously to H. Hart, S. Shamouilian, Y. Takehira, J. Org. Chem. 46 (1981) 4427;
   c) substituted monohalobenzenes and strong bases with elimination of hydrogen halide, for example analogously to P. G. Sammes, D. J. Dodsworth, J. C. S. Chem. Commun. 1979, 33;
   d) substituted anthranilic acid derivatives and isoamyl nitrile, for example analogously to C. W. Jefford, R.

McCreadie, P. Müller, B. Siegfried, J. Chem. Educ. 48 (1971) 708;

e) a review of the preparation of a series of substituted dehydroaromatic compounds is given in Houben-Weyl, Methoden der Organischen Chemie [Methods of Organic Chemistry], 4th Edition 1981, Volume V/2b, pp. 615, Georg-Thieme-Verlag, Stuttgart.

2. Synthesis by deamination of substituted anthracene-9,10-imines, for example analogously to L. J. Kricka, J. M. Vernon, J. C. S. Perkin I, 1973, 766.

3. Synthesis by cycloaddition of substituted 1,4-quinones with substituted anthracene derivatives, for example analogously to E. Clar, Chem. Ber. 64 (1931) 1676; W. Theilacker, U. Berger-Brose, K. H. Beyer, Chem. Ber. 93 (1960) 1658; P. D. Bartlett, M. J. Ryan, J. Am. Chem. Soc. 64 (1942) 2649; P. Yates, P. Eaton, J. Am. Chem. Soc. 82 (1960) 4436. V. R. Skvarchenko, V. K. Shalaev, E. I. Klabunovskii, Russ. Chem. Rev. 43 (1974) 951.

Further syntheses of substituted triptycenes are given by way of example in C. F. Wilcox, F. D. Roberts, J. Org. Chem. 30 (1965) 1959; T. H. Regan, J. B. Miller, J. Org. Chem. 32 (1967) 2798.

Further syntheses of heterotriptycenes are given, for example, in D. Hellwinkel, W. Schenk, W. Blaicher, Chem. Ber. 111 (1978) 1798; or D. Hellwinkel, W. Schenk, Angew. Chem. 24 (1969) 1049; N.P. McCleland, J. B. Withworth, J. Am. Chem. Soc. (1927) 2753; N. A. A. Al-Jabar, A. G. Massey, J. Organomet. Chem. 287 (1985) 57.

Compounds of the formula (III) can be synthesized, for example, starting from a substituted bistriptycene parent compound or heterobistriptycene parent compound, which is in turn accessible via various synthetic routes. The following may be mentioned by way of example, but not in a restrictive manner:

1) synthesis from substituted anthracene (or substituted acridine or substituted phenazine) and substituted didehydrobenzenes, for example analogously to H. Hart, S. Shamouilian, Y. Takehira J. Org. Chem. 46 (1981) 4427;

2) synthesis by cycloaddition of substituted anthracene derivatives with 1,4-benzoquinone, for example analogously to E. Clar, Chem. Ber. 64 (1931) 1676; P. Yates, P. Eaton, J. Am. Chem. Soc. 82 (1960) 4436; W. Theilacker, U. Berger-Brose, K. H. Beyer, Chem. Ber. 93 (1960)1658.

Further syntheses are given by way of example in H. Hart, A. Bashir-Hashemi, J. Luo, M. A. Meador, Tetrahedron 42 (1986) 1641; V. R. Skvarchenko, V. K. Shalevb, E. I. Klabunovskii, Russ. Chem. Rev. 43 (1974) 951; V. R. Skvarchenko, A. G. Shil'nikova, N. N. Konrat'eva, R. Ya. Levina, J. Org. Chem. USSR (Engl.trans.) 3 (1967) 1477.

The further functionalization of the parent compounds described above can be carried out, for example, starting from the corresponding 1,4-dialkyl or 1,4-dimethyl derivatives, the corresponding groups for the synthesis of the groups A and B in the compounds of the general formulae (II) and (III) being formed by halogenation or oxidation to the aldehyde or carboxylic acid. The following syntheses may be mentioned by way of example: Zaug, Rapalla, Org. Synth. 27 (1947) 84; Trahanovsky, Young, J. Org. Chem. 31 (1996) 2033; San Filippo, J. Org. Chem. 42 (1977) 2182; Ėtard, Ann., Chim. Phys. 22 (1881) 218; Sharpless J. Am. Chem. Soc. 97 (1975) 5927.

Introduction of groups for the synthesis of the groups A and B in the compounds of the general formulae (II) and (III) can likewise be achieved starting from the triptycene- or bistriptycenequinones. Thus, reaction of the quinones with organometallic reagents with subsequent didehydroxylation enables the introduction of various groups, such as, for example, alkyl, aryl or alkynyl. The following may be mentioned as examples of correspondingly analogous reactions: T. Imamoto, N. Takiyama, K. Nakamura, T. Hatajima, Y. Kamiya, J. Am. Chem. Soc., 111 (1989) 4392; A. Fischer, G. N. Henderson, Tetrahedron Lett. 24 (1983) 131; H. M. Crawford, J. Am. Chem. Soc. 70 (1948) 1081; C. T. Wigal, J. D. McKinley, J. Coyle, D. J. Porter, D. E. Lehman, J. Org. Chem. 60 (1995) 8421; or the corresponding chapters in Houben-Weyl, Methoden der Organischen Chemie [Methods of Organic Chemistry], Georg-Thieme-Verlag, Stuttgart. For the didehydroxylation, which can be carried out very effectively using low-valence titanium or tin or phenylhydrazine, reference can be made by way of example to the following: G. Solladie, A. Girardin, J. Org. Chem. 54 (1989) 2620 or M. lyoda, T. Yamauchi, M. Oda, J. C. S. Chem. Commun., 1986, 303; K. J. Clark, J. Chem. Soc. (1956) 1511.

Starting from the triptycene- or bistriptycenehydroquinones, after conversion into the corresponding triflates, mesylates or nonaflates, both palladium-catalyzed coupling or polymerization can be carried out, for example using organotin compounds analogously to Z. Bao, W. K. Chan, L. Yu, J. Am. Chem. Soc. 117 (1995) 12426; A. M. Echavarren, J. K. Stille, J. Am. Chem. Soc 109 (1987) 5478. K. Ritter, Synthesis (1993) 735. Furthermore, the triflates or mesylates, which are readily accessible from the hydroquinones, can also be coupled with organoboronic acids, for example analogously to T. Oh-e, N. Miyaura, A. Suzuki, Synlett (1990) 221; A. R. Martin, Y. Yang, Acta Chem. Scand. 47 (1993) 221; J. M. Fu, V. Sniekus, Tetrahedron Lett. 29 (1988) 1665; V. Percec, S. Okita, J. Polym. Sci. A 31 (1993) 877. In addition, the triflates and mesylates are starting materials for nickel-catalyzed C-C coupling, for example analogously to V. Percec, J. Y. Bae, M. Zhao, D. H. Hill, J. Org. Chem. 60 (995) 176; V. Percec, C. Pugh, E. Cramer, S. Okita, R. Weiss; Macromol. Symp. 54/55 (1992) 113. V. Percec, S. Okita, R. Weiss, Macromolecules 25 (1992) 1816; Y. Yamashita, Y. Inoue, T. Kondo, H. Hashimoto, Chem.Lett. (1986) 407;

For the synthesis of the groups A and B, reference may furthermore be made, for example, to J. S. Schumm, D. L. Pearson, J. M. Tour, Angew.Chem. 106 (1994) 1445; or to DE-A 23 44 732, 24 50 088, 24 29 093, 25 02 904, 26 36 684, 27 01 591 and 27 52 975 for compounds containing 1,4-phenylene groups, DE-A 26 41 724 for compounds containing pyrimidine-2,5-diyl groups; DE-A 40 26 223 and EP-A 0 391 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981) 513 to 519, DE-C-3 930 663, M. J. Sharp, W. Cheng, V. Snieckus in Tetrahedron Letters 28 (1987), 5093; G. W. Gray in J. Chem. Soc. Perkin Trans II, (1989) 2041 and Mol. Cryst. Liq. Cryst. 172 (1989) 165, Mol. Cryst. Liq. Cryst. 204 (1991) 43 and 91; EP-A 0 449 015; WO 89/12039; WO 89/03821; EP-A 0 354 434 for the direct linking of aromatics and heteroaromatics.

The preparation of disubstituted pyridines, disubstituted pyrazines, disubstituted pyrimidines and disubstituted pyridazines is described, for example, in the corresponding volumes of the series "The Chemistry of Heterocyclic Compounds" by A. Weissberger and E. C. Taylor (editors).

The compounds of the formula (I) according to the invention are suitable for use as electroluminescent materials.

For the purposes of the present invention, the term "electroluminescent materials" is taken to mean materials which are used as or in an active layer in an electroluminescent device. The term "active layer" means that the layer is capable of emitting light on application of an electric field (light-emitting layer) and/or that it improves the injection and/or transport of positive and/or negative charges (charge-injection or charge-transport layer). In addition, use as an electron-blocking layer or hole-blocking layer is also an application in accordance with the invention.

The invention therefore also relates to the use of a triptycene derivative of the formula (I) as electroluminescent material.

In order to be used as electroluminescent materials, the triptycene derivatives of the formula (I) are generally applied to a substrate in the form of a film by known methods familiar to the person skilled in the art, such as dipping, spin coating, vapor deposition or buffering under reduced pressure.

The invention thus likewise relates to an electroluminescent device having one or more active layers, where at least one of these active layers contains one or more triptycene derivatives of the formula (I). The active layer can be, for example, a light-emitting layer and/or a charge-transport layer and/or a charge-injection layer. The general construction of electroluminescent devices of this type is described, for example, in U.S. Pat. No. 4,539,507 and U.S. Pat. No. 5,151,629.

They usually contain an electroluminescent layer between a positive electrode and a negative electrode, where at least one of the electrodes is transparent to at least part of the visible spectrum. In addition, one or more electron-injection and/or electron-transport layers can be introduced between the electroluminescent layer and the negative electrode and/or one or more hole-injection and/or hole-transport layers can be introduced between the electroluminescent layer and the positive electrode. Suitable negative electrodes are preferably metals or metal alloys, for example Ca, Mg, Al, In or Mg/Ag. The positive electrodes can be metals, for example Au, or other metallically conducting substances, such as oxides, for example ITO (indium/tin oxide), on a transparent substrate, for example made of glass or a transparent polymer.

In operation, the negative electrode is set to a negative potential compared with the positive electrode. Electrons are injected by the negative electrode into the electron-injection layer/electron-transport layer or directly into the light-emitting layer. At the same time, holes are injected by the positive electrode into the hole-injection layer/hole-transport layer or directly into the light-emitting layer.

The injected charge carriers move through the active layers toward one another under the effect of the applied voltage. This results in electron/hole pairs recombining at the interface between the charge-transport layer and the light-emitting layer or within the light-emitting layer with emission of light. The color of the emitted light can be varied by means of the materials used as light-emitting layer.

Electroluminescent devices are used, for example, as self-illuminating display elements, such as control lamps, alphanumeric displays, signs and in opto-electronic couplers.

Compounds of the formula (I) are furthermore suitable, for example, for use in optical storage media, as photorefractive materials, for nonlinear optical (NLO) applications, as optical brighteners and radiation converters and, preferably, as hole-transport materials in photovoltaic cells, as described, for example, in WO-A 97/10 617 and DE-A 197 11 713, which are expressly incorporated herein by way of reference.

The invention is explained in greater detail by the examples, without this being intended to represent a limitation.

EXAMPLE 1

Synthesis of Dihydrotriptycene-1,4-quinone 17.8 g (100 mmol) of anthracene and 10.8 g (100 mmol) of p-benzoquinone (freshly sublimed) were dissolved in 200 ml of p-xylene at 135° C. under a nitrogen blanket. After a few minutes, a yellow, crystalline precipitate began to deposit from the now-red solution. After 4 hours, the mixture was allowed to cool to room temperature, and the precipitate was filtered off with suction. The yellow solid was rinsed with p-xylene and dried under reduced pressure. The resultant 26.0 g (91 mmol, 91%) were heated at 130° C. for 0.5 hour in 100 ml of p-xylene under $N_2$, cooled to room temperature, filtered off with suction, rinsed with methanol and dried, giving 23.5 g (82 mmol, 82%) of dihydrotriptycene-1,4-quinone as pale-yellow crystals.

Melting point: 232° C. $^1$H NMR: (400 MHz; $CDCl_3$): δ [ppm]=3.15 (t, 2H, tert. H), 4.86 (s, 2H, enyl-H), 6.30 (s, 2H, bridgehead-H) 7.07 and 7.39 (4H, m, J=5.3 Hz, 2.3 Hz -phenyl-H), 7.17–7.20 ppm, m, 4H, phenyl-H).

EXAMPLE 2

Synthesis of 1,4-Triptycene-1,4-quinone 37.0 g (129 mmol) of dihydrotriptycene-1,4-quinone were suspended in 350 ml of glacial acetic acid, and 1.5 ml of HBr (48% strength in water) were added at the boiling point. The mixture was refluxed for two hours. A solution of 13.0 g of $KIO_3$ (60 mmol) was then added dropwise at the boiling point over the course of 5 minutes. A yellow coloration of the suspension immediately becomes apparent. The mixture was allowed to cool, 200 ml of water were added at 50° C., and the solid was filtered off with suction, washed a number of times with $Na_2SO_3$ solution and then a number of times with water and dried under reduced pressure. The crude product (35.2 g, 96%) was triturated twice for one hour each time with 150 ml of isopropanol, giving 30.9 g (108.7 mmol, 84%) of 1,4-triptycene-1,4-quinone as a fluorescent-yellow, powdery substance.

Melting point: 273–275° C. $^1$H NMR: (400 MHz; $CDCl_3$): δ [ppm]=5.79 (s, 2H, bridgehead-H), 6.59 (s, 2H, enyl-H), 7.03 and 7.42 (m, 8H, J=2.3 Hz, 5.3 Hz, AB system phenyl-H)

EXAMPLE 3

Synthesis of 1,4-Dihydroxy-1,4-dimethyltriptycene 148 ml (237 mmol, 2.7 eq) of a 1.6 M solution of methyllithium in diethyl ether were introduced into a 1 l four-necked flask together with 300 ml of THF (distilled from Na/benzophenone), and the mixture was cooled to −78° C. (acetone/dry ice). At the same time, a solution of 25.0 g (87.9 mmol) of 1,4-triptycene-1,4-quinone in 600 ml of THF was cooled to the same temperature. The solution of 1,4-triptycene-1,4-quinone was transferred into a dropping funnel which was additionally cooled by means of dry ice. The starting-material solution was slowly added dropwise (1 hour) with vigorous stirring, the solution immediately changing color to blue/blue-green. When the addition was complete, the temperature was maintained for a further hour and the cooling was then removed. The mixture was allowed to warm to room temperature and was stirred overnight.

The suspension was evaporated to about 200 ml under reduced pressure and then poured into a mixture of 1.4 l of ice-water and 10 g of $NH_4Cl$. During the pouring-in, heat was evolved and a pale-beige precipitate deposited; this liquefied on warming to room temperature. The resultant oil was separated off, and the water phase was extracted 3×with 500 ml of $CH_2Cl_2$. The combined organic phases were washed twice with 200 ml of water each time, dried using $Na_2SO_4$ and evaporated as far as possible on a rotary evaporator.

A brown, viscous material remained which was treated with 30 ml of diethyl ether/hexane 2:1 in an ultrasound bath until all the oil had dissolved and a white precipitate had formed. The precipitate was filtered off with suction, and the mother liquor was re-evaporated on a rotary evaporator and treated in the same way, with the volumes of the $Et_2O$/hexane mixture always being selected somewhat smaller. An analogous procedure was followed until precipitate no longer deposited. For further purification, the reaction mixture was refluxed in diethyl ether, cooled to 20° C. and filtered off with suction, giving 14.9 g (47.1 mmol, 54%) of 1,4-dihydroxy-1,4-dimethyltriptycene as a white powder.

$^1$H NMR: (400 MHz; DMSO-$d_6$): δ=1.09 (s, 6H, methyl-H); 4.84 (s, 2H, hydroxy-H); 5.34 (s, 2H, quinone-H); 5.63 (s, 2H, bridgehead-H); 6.90, 6.92, 7.28, 7.33 (m, each 2H, J=5.3 Hz and 2.3 Hz, phenyl-H).

$^1$H NMR: (400 MHz; $CDCl_3$): δ=1.27 (s, 6H, methyl-H); 1.63 (s, 2H, hydroxy-H); 5.39 (s, 2H, quinone-H); 5.54 (s, 2H, bridgehead-H); 6.91 (m, 2H, J=5.5 Hz and 2.3 Hz, phenyl-H); 6.95 (m, 2H, J=5.3 Hz and 2.0 Hz, phenyl-H); 7.32 (m, 4H, J=5.3 Hz, 2.3 Hz and 2.0 Hz, phenyl-H).

EXAMPLE 4

Synthesis of 1,4-Dimethyltriptycene 6.70 g (53.3 mmol, 2.1 eq) of $SnCl_2.2 H_2O$ were dissolved in 200 ml of 50% strength acetic acid. A methanolic solution of 8.44 g (25.7 mmol) of 1,4-dihydroxy-1,4-dimethyltriptycene was slowly added dropwise at such a rate that the temperature did not rise above a maximum of 45° C. The reaction solution became yellowish, and a white precipitate deposited. When the addition was complete, the mixture was stirred at room temperature for a further 2 hours and then cooled to −18° C., and the resultant precipitate was filtered off with suction, washed acid-free with about 1 l of water and dried under reduced pressure. The mother liquor obtained was then evaporated somewhat in a rotary evaporator, and the precipitate obtained after re-cooling was again filtered off with suction, giving 7.0 g of crude product. The compound was dissolved in about 300 ml of boiling acetone and subsequently precipitated using 50 ml of water. The solution was cooled in an icebox, and the precipitate was filtered off with suction. Repetition of this procedure gave 5.20 g (18.4 mmol, 72%) of 1,4-dimethyltriptycene as white crystal flakes.

Melting point: 246–249° C. $^1$H NMR: (400 MHz; DMSO-$d_6$): δ=2.43 (s, 6H, methyl-H); 5.80 (s, 2H, bridgehead-H); 6.71 (s, 2H, phenyl-H); 6.98 and 7.45 (m, 8H, J=2.3 Hz, 5.3 Hz, AB system, phenyl-H).

$^1$H NMR: (400 MHz; $CDCl_3$): δ=2.46 (s, 6H, methyl-H); 5.64 (s, 2H, bridgehead-H); 6.70 (s, 2H, phenyl-H); 6.97 and 7.36 (m, 8H, J=2.3 Hz, 5.3 Hz, AB system, phenyl-H).

EXAMPLE 5

Synthesis of 1,4-bis(Bromomethyl)triptycene 4.9 g (17.5 mmol) of dimethyltriptycene were dissolved in 150 ml of dry tetrachloromethane, and 7.2 g (40 mmol) of NBS and 1 mol % of AZIBN were added. The suspension was refluxed gently with irradiation by an Hg lamp and then allowed to cool, and the succinimide was separated off. The tetrachloromethane solution was evaporated in a rotary evaporator, and the residue was recrystallized twice from acetonitrile, giving 7.7 g (96%) of colorless 1,4-bis (bromomethyl)triptycene of melting point 198–204° C.

$^1$H NMR; 400 MHz/$CDCl_3$: δ/ppm=4.67 (s, 4H), 5.4 (s, 2H), 6.9 (s, 2H), 7.02 and 7.47 (each m, each 4H); IR (KBr): ν/cm$^{-1}$: 3034, 2987, 1460, 1444, 1403, 1202, 822, 716, 616; MS: (FD, 8 kV); m/e:439.9 (100%), [M$^+$].

EXAMPLE 6

Synthesis of 6,11-Dioxo-5,5a,11a,12-tetrahydro-5,12-o-ben-zenonaphthacene 45.0 g (250 mmol) of anthracene and 40.0 g (250 mmol) of pre-purified ($Et_2O$/activated carbon) 1,4-naphthoquinone were suspended in 700 ml of dry $CHCl_3$ in a 2000 ml two-necked flask and cooled to 0° C. using ice. 34.7 g (260 mmol) of anhydrous aluminum chloride were subsequently added to the suspension in one portion, during which the reaction solution changed color from reddish at the beginning to deep blue. When the addition was complete, the ice bath was removed. A color change to pale beige to green was immediately detectable. The mixture was stirred at room temperature for a further 2 hours. 500 ml of $CHCl_3$ were then added, and the reaction solution was poured into 700 ml of ice/water.

The ochre precipitate which deposited during this operation was re-dissolved by addition of as little chloroform as possible at room temperature. The phases were separated in a separating funnel, the water phase was extracted twice with 200 ml of $CHCl_3$ each time, washed, 2×with 100 ml of saturated sodium hydrogencarbonate solution and 1×with 100 ml of sodium chloride solution, and the combined extracts were dried over anhydrous $Na_2SO_4$. During evaporation of the solvent, 400 ml of MeOH were added at the point when crystallization begins, whereupon the product crystallized out.

Re-dissolution in chloroform and precipitation using methanol gave 84.0 g (96%) of colorless, crystalline 6,11-dioxo-5,5a,11a,12-tetrahydro-5,12-o-benzenonaphthacene of melting point 207–208° C.

$^1$H-NMR; 400 MHz/$CDCl_3$: δ=3.37 (t, 2H), 5.00 (s, 2H), 7.10–7.12, 7.18–7.20, 7.42–7.45, 7.54–7.56, 7.83–7.86 (each m, 2H); IR (KBr): ν/cm$^{-1}$: 3063, 3020, 2963, 1676, 1589, 1467, 1270, 1005, 758, 727, 574.

EXAMPLE 7

Synthesis of 6,11-Dioxo-5,12-dihydro-5,12-o-benzeno-naphthacene(naphthotriptycene-6,11-quinone)

16.0 g (47.5 mmol) of dihydronaphthotriptycene-6,11-quinone were dissolved in 500 ml of boiling glacial acetic acid in a 1 l flask, and 1.5 ml of 48% strength HBr in water were added. After the mixture had been kept at 100° C. for about 25 minutes, a solution of 2.65 g (15.8 mmol) of potassium bromate in 120 ml of water was slowly added dropwise. During the dropwise addition, a color change to yellow initially occurred, but this was immediately accompanied by blackening of the resultant suspension together with thickening of the reaction mixture. When all the $KBrO_3$ had been added, the mixture was kept at 100° C. for a further 5 hours. The color changed to yellow. The hot mixture was then made up to a volume of 1000 ml using water, and the heating bath was removed. The mixture was cooled to room temperature, and the product was filtered off with suction, washed with water until neutral and dried, giving 15.0 g (94%) of naphthotriptycene-6,11-quinone as fluorescent-yellow microcrystals.

Melting point: 295–300° C. $^1$H NMR (CDCl$_3$, 400 MHz): d=6.00 (s, 2H, bridgeheads); 7.03–7.05 (m, 4H, phenyl-H); 7.45–7.47 (m, 4H, phenyl-H); 7.64–7.67 (m, 2H, phenyl-H); 8.03–8.06 (m, 2H, phenyl-H).

EXAMPLE 8

Synthesis of 6,11-Dihydroxy-6,11-dimethyl-5,12-dihydro-5,12-o-benzenonaphthacene 210 ml (470 mmol) of methyllithium (2.2 M in ether/hexane) were introduced into a 2 l four-necked flask together with 50 ml of THF, and the mixture was cooled to −78° C. using acetone/dry ice. 60.0 g (180 mmol) of 6,11-dioxo-5,5a,11a,12-tetrahydro-5,12-o-benzenonaphthacene in 700 ml of THF were slowly added dropwise to this mixture with vigorous stirring. After the addition, the mixture was kept at low temperature for three hours, then allowed to warm to room temperature over the course of three hours and stirred at room temperature for a further two hours. About 400 ml of THF were distilled off under reduced pressure, and the suspension was poured into 2.5 l of water/ice (2:1) in which 30 g of NH$_4$Cl had been dissolved, so that approximately pH 8 was maintained. The precipitated crude product was filtered off with suction and dried. Recrystallization twice from acetone/water gave 60.4 g (79%) of colorless 6,11-dihydroxy-6,11-dimethyl-5,12-dihydro-5,12-o-benzenonaphthacene of melting point 255–260° C. (decomp.).

$^1$H-NMR; 400 MHz/CDCl$_3$: δ=1.40 (s, 6H), 1.82 (s, 2H), 5.55 (s, 2H), 6.92–6.94 (m, 2H), 6.97–6.99 (m, 2H), 7.25–7.28 (m, 2H), 7.34–7.38 (m, 4H), 7.58–7.60 (m, 2H); IR: ν/cm$^{-1}$: 3582, 3400–3200, 3066, 3016, 2973, 2920, 1456, 1228, 918, 761, 652.

EXAMPLE 9

Synthesis of 6-Hydroxymethyl-11-methyl-5,12-dihydro-5,12-o-benzenonaphthacene(6-methyl-11-hydroxymethylnaphthotriptycene) and 6-Chloromethyl-11-methyl-5,12-dihydro-5,12-o-benzenonaphthacene (6-Methyl-11-chloromethylnaphthotriptycene)

76 ml (145 mmol) of TiCl$_3$ solution (1.9 M in 2N HCl) were introduced into a 500 ml three-necked flask under N$_2$ and stirred in an acetone/ice mixture (−10° C.). A solution of 13.3 g (36.3 mmol) of naphthotriptycene-6,11-dimethyl-6,11-diol in 200 ml of DME was added dropwise via a dropping funnel. After about 5 minutes, a white precipitate started to deposit from the solution and floated on the reaction mixture. After five hours at room temperature, a TLC showed two spots corresponding to the hydroxymethyl and chloromethyl compounds. The precipitated 6-methyl-1 1-chloromethyl-naphthotriptycene was filtered off with suction, giving 9.3 g (70%) of crude product.

The phases of the filtrate were separated, and the organic phase was washed with 2N HCl, dried (Na$_2$SO$_4$) and evaporated in a rotary evaporator. The residue which remained was dissolved in methylene chloride and again shaken with 2N HCl. This procedure was carried out until any cloudiness present has disappeared (6 times). After drying Na$_2$SO$_4$), sufficient methylene chloride was stripped off until everything just remained in solution at the boiling point. A further 1.7 g (13%) of a mixture of 6-methyl-11-hydroxymethylnaphthotriptycene and 6-methyl-11-chloromethylnaphthotriptycene were obtained.

This mixture was converted into 6-methyl-11-chloromethylnaphtho-triptycene by refluxing for four hours in a solution of 4N HCl in dioxane and then precipitating the cooled solution using cold 2N HCl. The compound was recrystallized from methylene chloride/hexane.

Pure 6-methyl-11-hydroxymethylnaphthotriptycene was obtained by stirring for several hours in N-methylpyrrolidone/water (2:1) at 90° C.

6-Methyl-11-chloromethylnaphthotriptycene:

Melting point: 308–312° C. $^1$H NMR (DMSO-d$_6$, 400 MHz): d=2.83 (s, 3H, methyl-H), 5.60 (s, 2H, methylene-H), 6.18, 6.26 (s, each 1H, bridgeheads), 7.03–7.07 (m, 4H, phenyl-H), 7.50–7.58 (m, 6H, phenyl-H), 8.00–8.03 (m, 1 H, naphthyl-H), 8.08–8.11 (m, 1H, naphthyl-H)

$^1$H NMR (CDCl$_3$, 400 MHz): d=2.83 (s, 3H, methyl-H), 5.31 (s, 2H, methylene-H), 5.91, 5.93 (s, each 1H, bridgeheads), 7.03–7.06 (m, 4H, phenyl-H), 7.41–7.48 (m, 6H, phenyl-H), 7.94–7.96 (m, 1H, naphthyl-H), 7.99–8.01 (m, 1H, naphthyl-H) Mass: m/e: 365.9 (M$^+$)

6-Methyl-1-hydroxymethylnaphthotriptycene:

Melting point: 316° C. $^1$H NMR (CDCl$_3$, 400 MHz): d=2.80 (s, 3H, methyl-H), 5.17 (s, 2H, methylene-H), ), 5.18 (s, 1H, hydroxy-H), 6.14, 6.17 (s, each 1H, bridgeheads), 7.02–7.04 (m, 4H, phenyl-H), 7.45–7.47 (m, 2H, phenyl-H), 7.51–7.53 (m, 4H, phenyl-H), 7.95–7.98 (m, 1H, naphthyl-H), 8.15–8.17 (m, 1H, naphthyl-H) IR: ν/cm$^{-1}$=3700–3300, 3000–3100, 2980, 1450, 760.

EXAMPLE 9a

Synthesis of 6-Chloromethyl-11-methyl-5,12-dihydro-5,12-o-benzenonaphthacene

Analogous performance of the reaction in EXAMPLE 9, with the difference that the reaction time was 48 hours at room temperature and subsequently a further 5 hours under reflux. The colorless solid was then separated off, rinsed with diethyl ether and semiconcentrated hydrochloric acid, dissolved in chloroform and washed with 5N HCl until the violet coloration had been removed, and the organic phase was separated off, dried and evaporated in a rotary evaporator, giving 12 g (83%) of colorless crude product. The solid was re-dissolved in boiling CH$_2$Cl$_2$ and crystallized using hexane, giving 10 g (76%) of pure, colorless 6-chloromethyl-11-methyl-5,12-dihydro-5,12-o-benzenonaphthacene of melting point 308–312° C.

EXAMPLE 10

Synthesis of 6-Formyl-11-methyl-5,12-dihydro-5,12-o-benzenonaphthacene (6-carboxy-11-naphthotriptycene)

A solution of 2.85 g (7.0 mmol) of sodium dichromate dihydrate in 60 ml of water and 30 ml of sulfuric acid (about 3 molar) was slowly added dropwise at 0° C. with stirring to a solution of 10 g (28.7 mmol) of 6-hydroxymethyl-11-methyl-5,12-dihydro-6,11-o-benzenonaphthacene and 2.85 g (7.0 mmol) of tetrabutylammonium hydrogensulfate in 350 ml of CH$_2$Cl$_2$. When the addition was complete, the mixture was stirred at room temperature for a further hour.

The mixture was transferred into a separating funnel, and the phases were separated. The water phase was extracted three times with methylene chloride (50 ml). The combined organic phases were washed twice with 50 ml of aqueous NaCl solution and once with pure water and subsequently dried over sodium sulfate. After evaporation in a rotary evaporator, 10 g (100%) of crude product were isolated. The crude product was dissolved in dimethoxyethane and precipitated at the boiling point using water, giving 9.0 g (90%) of virtually colorless 6-formyl-11-methyl-5,12-dihydro-5, 12-o-benzenonaphthacene of melting point 246–248° C.

$^1$H-NMR; 400 MHz/DMSO: δ=2.91 (s, 3H, methyl-H) 6.3/6.9 (s, each 1H), 6.9–7.10 (m, 4H), 7.55–7.59 (m, 6H), 8.07–8.09 (m, 2H), 8.92–8.94 (m, 2H), 11.25 (s, 1H); IR(KBr): v/cm$^{-1}$: 3068, 3020, 2870, 1676, 1571, 1463, 1160, 763, 637, 578.

EXAMPLE 11

Synthesis of 2,5-bis((6,11-Dihydro-6,11-o-benzeno-12-methylnaphthacene)-5-yl)-1,3,4-oxadiazol (triptycene-BNP)

0.70 g (2.55 mmol) of 6-carboxy-11-methylnaphthotriptycene were suspended in 0.5 ml of dry N,N-dimethylformamide in a 100 ml two-necked flask with exclusion of moisture, and 10 ml of freshly distilled thionyl chloride were added. The evolution of gas which immediately commenced had subsided after 15 minutes; the solution was subsequently refluxed for 7 hours. The N,N-dimethylformamide and the excess thionyl chloride were distilled off under reduced pressure, and the residue was stirred up three times with 30 ml of petroleum ether (90° C.) in each case and again distilled off. The yellowish acid chloride obtained was then dissolved in 20 ml of dry 1,4-dioxane, and the solution was divided up. 10 ml of this solution were slowly added dropwise at room temperature to a solution of 1.5 ml of hydrazine hydrate (80%) in 25 ml of dioxane, and the mixture was stirred for a further 1 hour. The reaction mixture was subsequently poured into 100 ml of water, and the precipitated carbohydrazide was filtered off with suction and dried. Yield: 304 mg (64%)

$^1$H NMR (CDCl$_3$, 400 MHz): d=2.83 (s, 3H, methyl-H), 4.77 (s, 2H, terminal amine-H), 5.64 and 6.18 (2×s, each 1H, bridgehead-H), 6.98–7.10 (m, 4H, phenyl-H), 7.40–7.60 (m, 6H, phenyl-H), 7.66–7.68 (m, 1H, naphthyl-H), 7.98–8.00 (m, 1H, naphthyl-H), 9.58 (s, 1H, amine-H).

The resultant carbohydrazide was dissolved in 25 ml of dry pyridine and added, with vigorous stirring at room temperature, to the remaining 10 ml of the solution of the acid chloride in dioxane, and the mixture was refluxed for 2 hours. The still-warm solution was poured into 200 ml of water and stirred briefly. 200 ml of methylene chloride were subsequently added, and the water phase was acidified using 18% strength HCl. The phases were separated, and the water phase was extracted a further three times with 30 ml of CH$_2$Cl$_2$. The combined organic phases were washed with 2N HCl and water, dried over sodium sulfate and evaporated in a rotary evaporator. The crude ditriptycenenaphthoyl hydrazine obtained in this way was then refluxed for four hours in 30 ml of freshly distilled thionyl chloride. The reaction solution was subsequently slowly added dropwise to a mixture of 200 ml of ice/50 ml of water. The resultant precipitate was filtered off with suction, dried and recrystallized from DME, giving 255 mg of 2,5-bis((6,11-dihydro-6,11-o-benzeno-12-methylnaphtacene)-5-yl)-1,3,4-oxadiazole as a blue-fluorescent substance.

Melting point 366° C.; on cooling, the melt solidifies in a glass-like manner. $^1$H NMR (DMSO-d$_6$, 400 MHz): d=2.98 (s, 6H, methyl-H), 6.06 and 6.36 (2×s, each 2H, bridgehead-H), 7.02–7.12 (m, 8H, phenyl-H), 7.40–7.60 (m, 6H, phenyl-H), 7.48–7.50 (d, 4H, naphthyl-H), 7.63–7.65 (m, 6H, phenyl-H), 7.93–7.95 (m, 2H, naphthyl-H), 8.16–8.17 (m, 2H, naphthyl-H). Mass: FD, m/e=701.9 (M$^+$), 350.8 (M$^{++}$) UV-VIS: Absorption: $\lambda_{max}$=274 nm Emission: 408 nm (solution 10$^{-5}$ mol/l), 410 nm (film) Cyclic voltammetry: Reduction; 0.1M TBAHFP/THF, (Fc/Fc$^+$), 100 mV/s: $E_{11/2}$=−2553 mV, $E_{21/2}$=−2811 mV.

EXAMPLE 12

Synthesis of Naphthotriptycene-6,11-dicarboxylic Acid 2.0 g of 6-hydroxymethyl-11-methylnaphthotriptycene (5.7 mmol), a solution of 0.5 g (12.5 mmol) of NaOH in 20 ml of water and 0.1 g (0.25 mmol) of tetrabutylammonium hydrogensulfate were dissolved in 130 ml of CH$_2$Cl$_2$, and a solution of 3.0 g (19 mmol) of potassium permanganate in 50 ml of water was added dropwise at room temperature with stirring. The solution changes color to blue, and a brown precipitate deposits. The addition was carried out over the course of 1.5 hours at such a rate that the temperature of the mixture did not exceed 40° C. The mixture was then stirred at room temperature for a further 24 hours.

The resultant manganese dioxide was then filtered off and washed with a little 2N NaOH and 2×with 10 ml of methylene chloride. The phases were separated, and the organic phase was extracted 3×with 20 ml of 2N NaOH. The basic water phase was washed 2×with 20 ml of diethyl ether. Semiconcentrated HCl was then added dropwise until a pH of about 2–3 had been reached. At pH 6, the acid began to precipitate from the solution. The water phase was then extracted 3×with 30 ml of ethyl acetate, and the organic phase was dried and evaporated to about 30 ml. After warming to about 60° C., hexane was then added until a white precipitate only dissolved slowly. The mixture was cooled in the refrigerator and the resultant crystalline precipitate was filtered off with suction, giving 300 mg (14%) of naphthotriptycene-6,11-dicarboxylic acid.

Melting point: 310–316° C. $^1$H NMR (DMSO-d$_6$, 400 MHz): d=5.88 (s, 2H, bridgehead-H), 7.08–7.11 (m, 4H, phenyl-H), 7.48–7.50 (m, 4H, 4 phenyl-H), 7.57–7.60 (m, 2H, naphthyl-H), 7.88–7.91 (m, 2H, naphthyl-H), 13.96 (s, 2H, carboxyl-H)

EXAMPLE B8

Synthesis of 5,12-bis(5-p-tert-Butylphenyl-1,3,4-oxadiazol-2-yl)-6,11-dihydro-6,11-o-benzenonaphthacene 1.0 g (2.55 mmol) of naphthotriptycene-6,11-dicarboxylic acid was suspended in 2 ml of dry N,N-dimethylformamide at room temperature in a 200 ml two-necked flask with exclusion of moisture, and 10 ml of freshly distilled thionyl chloride were added. The evolution of gas which commenced immediately had subsided after 15 minutes. The solution was then refluxed for a further 3 hours. N,N-Dimethylformamide and excess thionyl chloride were distilled off under reduced pressure, and the residue was stirred up a further three times with 30 ml of petroleum ether (90° C.) in each case and re-distilled off under reduced pressure. The resultant yellowish acid chloride was then dissolved in 30 ml of pyridine (dried over molecular sieve), and a solution of 1.1 g (5.30 mmol) of p-tert-butylphenyltetrazole in 20 ml of pyridine was added, and the mixture was subsequently refluxed for 2 hours. The cooled solution was poured into 300 ml of water, and the resultant precipitate was filtered off with suction and dried. The resultant crude product was dissolved in chloroform and extracted twice with 100 ml of 2N HCl each time and washed with 100 ml of water. The organic phase was dried over $Na_2SO_4$ and evaporated in a rotary evaporator. Chromatography using hexane/EE 1:1 over silica gel gave 600 mg of colorless, strongly blue-fluorescent 5,12-bis(5-p-tert-butylphenyl-1,3,4-oxadiazol-2-yl)-6,11-dihydro-6,11-o-benzenonaphtacene.

Melting point 285° C.–288° C. $^1$H-NMR (400 MHz; DMSO-$d_6$): δ=1.38 (s, 18H, t-butyl-H), 6.15 (s, 2H, bridgehead-H), 7.13–7.15 (m, 4H, phenyl-H), 7.55–7.58 (m, 4H, phenyl-H), 7.63–7.65 (m, 2H, naphthyl-H), 7.75–7.78 (m, 4H, phenyl-H) 8.04–8.06 (m, 2H, naphthyl-H), 8.15–8.18 (m, 4H, phenyl-H).

EXAMPLE 13

Synthesis of 6-Bromomethyl-11-chloromethylnaphtho-triptycene 1.0 g (2.7 mmol) of 6-methyl-11-chloromethylnaphthotriptycene was suspended in 150 ml of dry tetrachloromethane and gently refluxed together with 0.5 g (2.7 mmol) of N-bromosuccinimide and 0.08 g (0.5 mmol) of diazoisobutyronitrile (AZIBN) with irradiation with a 500 W halogen lamp. After 3 hours, the mixture was allowed to cool to room temperature, and the precipitated succinimide was separated off by filtration. The mixture was evaporated to 60 ml and crystallized at 50° C. by addition of hexane. After cooling in the icebox, the precipitate was filtered off with suction and dried. Recrystallization from $CCl_4$/hexane gave 440 mg (44%) of 6-bromomethyl-1-chloromethylnaphthotriptycene as colorless crystals.

Melting point: 291–295° C. $^1$H NMR (CDCl$_3$, 400 MHz): d=5.19 (s, 2H, bromomethyl-H), 5.28 (s, 2H, chloromethyl-H), 5.95 (d, 2H, bridgehead-H), 7.06–7.10 (m, 4H, phenyl-H), 7.49–7.47 (m, 6H, 4 phenyl-H, 2 naphthyl-H), 8.01–8.03 (m, 2H, naphthyl-H).

EXAMPLE 14

Synthesis of 1-Formyl4-methylnaphthotriptycene 10 g (28.7 mmol) of 6-hydroxymethyl-11-methylnaphthotriptycene and 1.0 g (2.9 mmol) of tetrabutylammonium hydrogensulfate were dissolved in 200 ml of $CH_2Cl_2$, and a solution of 2.85 g (7.0 mmol) of sodium dichromate dihydrate in a mixture of 60 ml of water and 30 ml of sulfuric acid (=6M) was slowly added dropwise at 0° C. with stirring. When the addition was complete, the mixture was stirred at room temperature for a further three hours.

After the phases had been separated, the water phase was extracted three times with methylene chloride (50 ml) each time. The combined organic phases were washed 2×with 50 ml of water each time and subsequently dried over sodium sulfate. Evaporation in a rotary evaporator left 10.0 g (100%) of a yellow-green solid.

The crude product was recrystallized from glacial acetic acid. Drying gave 9.7 g (98%) of 1-formyl4-methylnaphthotriptycene as a yellow-green powder.

Melting point: 246–248° C. $^1$H NMR (DMSO-$d_6$, 400 MHz): d=2.91 (s, 3H, methyl-H) 6.30 and 6.90 (s, each 1H, bridgehead-H), 6.90–7.10 (m, 4H, phenyl-H), 7.55–7.59 (m, 6H, 4 phenyl-H, 2 naphthyl-H), 8.07–8.09 (m, 1H, naphthyl-H), 8.92–8.94 (m, 1H, naphthyl-H), 11.25 (s, 1H, aldehyde-H)

EXAMPLE 15

Synthesis of 6,11-diformylnaphthotriptycene 2.0 g (4.49 mmol) of 6-bromomethyl-11-chloromethylnaphthotriptycene were suspended in 30 ml of DMSO together with 3.0 g of sodium hydrogencarbonate, and the mixture was held at a temperature of 75–80° C. for three hours. The reaction mixture was subsequently poured into water and the resultant beige-yellow precipitate was filtered off with suction. After the precipitate had been dried, it was dissolved in as little boiling glacial acetic acid as possible and was slowly crystallized by cooling. Drying gave 0.60 g (1.67 mmol, 37%) of 6,11-diformylnaphthotriptycene as pale-yellow crystals. $^1$H NMR (DMSO-$d_6$, 400 MHz): d=6.80 (s, 2H, bridgehead-H), 7.11–7.13 (m, 4H, phenyl-H), 7.59–7.61 (m, 4H, phenyl-H) 7.65–7.67 (m, 2H, naphthyl-H), 8.71–8.74 (m, 2H, naphthyl-H), 11.26 (s, 2H, formyl-H).

EXAMPLE 16

Synthesis of 2,3,5,6-bis(9,10-dihydro-9,10-anthracenyl)-1,4-cyclohexadione 10.0 g (56 mmol) of anthracene and 3.02 g (28 mmol) of p-benzoquinone (freshly sublimed) were suspended in 150 ml of dried methylene chloride in a 500 ml three-necked flask with ice cooling under $N_2$. 3.72 g (28 mmol) of $AlCl_3$ were subsequently added. During the addition, the reaction solution changed color from initially reddish to deep blue. When the addition was complete, the ice bath was removed, and the mixture was stirred at room temperature for about a further 2.5 hours.

After this time, a further 100 ml of $CH_2Cl_2$ were added, and the reaction solution was poured onto ice, during which an ochre precipitate deposited; this re-dissolved in the methylene chloride at room temperature. The phases were separated in a separating funnel, the water phase was extracted twice with 25 ml of $CH_2Cl_2$, and the combined methylene chloride extracts were dried. Stripping-off of the solvent left 7.36 g (56%) of crude product as a brownish-beige residue.

For purification, the product was refluxed in 75 ml of xylene. The mixture was allowed to cool, and the precipitate was filtered off with suction.

Further recrystallization from dioxane gave 6.04 g (46%) of white product.

Melting point: 247° C.

EXAMPLE 17

Synthesis of Dihydrobistriptycenequinone 2.20 g (7.7 mmol) of triptycenequinone and 1.38 g (7.7 mmol) of anthracene were suspended in 100 ml of p-xylene in a 250 ml flask under a protective gas. On heating to the boiling point, a dark-yellow solution was formed from which yellow crystals began to precipitate after about 30 minutes. After about 4 hours, the mixture was allowed to cool to room temperature. The precipitate was filtered off with suction, rinsed with xylene and dried, giving 3.20 g (90%) of crude product (melting point: 298° C.). The substance was refluxed for about 20 minutes in p-xylene. Cooling and filtering off with suction gave 2.9 g (82%) of dihydrobistriptycenequinone as yellowish crystals.

Melting point: >345° C. $^1$H NMR (CDCl$_3$, 400 MHz): d=3.07 (m, 2H, alkyl-H), 4.70 (s, 2H, bridgehead-H), 5.53

(s, 2H, bridgehead-H), 6.35–6.39 and 6.81–6.85 (m, AB system, add. 4H, phenyl-H), 6.91–6.97 (m, 4H, phenyl-H), 7.13–7.19 (m, 4H, phenyl-H), 7.32–7.38 (m, 4H, phenyl-H).

EXAMPLE 18

Synthesis of Bistriptycenehydroquinone 2.06 g (4.5 mmol) of dihydrobistriptycenequinonone were suspended under $N_2$ in 50 ml of glacial acetic acid with addition of 1.5 ml of 48% strength aqueous hydrobromic acid, and the mixture was warmed to the reflux temperature. After reflux for a total of 4 hours, the mixture was allowed to cool, and the precipitate was filtered off with suction and washed with water until neutral. The bistriptycenehydroquinone was dried and stored with exclusion of oxygen and light; 1.74 g (84%) of crude product were obtained.

The substance obtained was recrystallized from isopropanol under $N_2$, giving 1.44 g (70%) of bistriptycenehydroquinone as a colorless crystalline substance.

Melting point: 270° C. (decomposition).

Synthesis of CN-Trp-BND

EXAMPLE 19

Synthesis of 6-Cyano-11-methyl-5,12-dihydro-5,12-o-benzeno-naphthacene 3 g (8.7 mmol) of 6-formyl-11-methyl-5,12-dihydro-5,12-o-benzenonaphthacene, 0.5 g (2.6 mmol) of p-toluenesulfonic acid, 0.7 g (10.0 mmol) of hydroxylammonium chloride and 5.0 g (41.0 mmol) of anhydrous magnesium sulfate were dissolved in 50 ml of p-xylene, and the mixture was heated at 130° C. for six hours. The reaction solution was then cooled to 50° C., 30 ml of chloroform were added, and the mixture was filtered through a fluted filter while still slightly warm. The magnesium sulfate separated off was rinsed with chloroform and discarded. The filtrate was evaporated in a rotary evaporator, and the resultant solid was held at 120° C. for 4 hours in 30 ml of acetic anhydride. The mixture was then cooled, during which crude, slightly brownish, blue-fluorescent product slowly crystallized out. The precipitate was filtered off with suction and rinsed with a little glacial acetic acid. The filtrate was again heated to 100° C., and 25 ml of water were added very carefully in small portions for partial hydrolysis of the acetic anhydride. During cooling, further product precipitated and was likewise filtered off with suction. Recrystallization of the combined solids from xylene gave 2.2 g (76%) of colorless 6-cyano-11-methyl-5,12-dihydro-5,12-o-benzenonaphthacene having a melting point of above 370° C.

$^1$H-NMR; 400 MHz/DMSO: δ/ppm=2.91 (s, 3H) 6.0 and 6.3 (s, each 1H), 7.10–7.12 (m, 4H), 7.59–7.68 m, 6H, 4-phenyl-H, 2-naphthyl-H), 7.93–7.96 (m, 1H), 8.06–8.08 (m, 1H);

$^1$H-NMR; 400 MHz/CDCl$_3$: δ/ppm=2.68 (s, 3H) 5.9 and 6.0 (s, each 1H), 7.05–7.10 (m, 4H), 7.41–7.56 (m, 6H), 7.92–7.94 (m, 1H), 8.06 (m, 1H); IR(KBr): v/cm$^{-1}$: 3042, 2950, 2212, 1580, 1462,1197, 1158, 765, 578;

EXAMPLE 20

Synthesis of 6-Cyano-11-bromomethyl-5,12-dihydro-5,12-o-benzenonaphthacene 2.1 g (5.8 mmol) of 6-cyano-11-methyl-6,11-dihydro-6,11-o-benzeno-naphthacene were heated to gentle reflux in 200 ml of dry tetrachloromethane at 90° C. under a nitrogen blanket in a 250 ml two-necked flask by irradiation with a mercury lamp. 1.24 g (7 mmol) of NBS and 50 mg (0.3 mmol) of diazoisobutyronitrile were mixed homogeneously. 0.25 g portions of this mixture were added to the reaction solution at intervals of 30 minutes. When the addition was complete, the mixture was refluxed for a further two hours.

The mixture was then firstly allowed to cool to room temperature, and insoluble succinimide was separated off. The tetrachloromethane solution was evaporated in a rotary evaporator, and the resultant solid was dissolved in as little chloroform as possible and precipitated at the boiling point using 100 ml of hexane. After the mixture had been cooled in the icebox, the precipitate was filtered off with suction and dried, giving 2.2 g (90%) of colorless powder of 6-cyano-11-bromomethyl-5,12-dihydro-5,12-o-benzenonaphthacene of melting point 308–315° C.

$^1$H-NMR: 400 MHz/CDCl$_3$: δ/ppm=5.14 (s, 2H), 5.93 and 6.0 (each s, each 1H), 7.08–7.13 (m, 4H), 7.51–7.57 (m, 4H), 7.59–7.63 (m, 2H), 8.00–8.02 (m, 1H), 8.1–8.14 (m, 1H); IR(KBr): v/cm$^{-1}$: 3069, 2970, 2850, 2216, 1512, 1462, 1207, 1158, 762, 575;

EXAMPLE 21

Synthesis of 6-Cyano-11-tosylmethyl-5,12-dihydro-5,12-o-benzenonaphthacene 1.0 g (2.4 mmol) of 6-cyano-11-bromomethyl-5,12-dihydro-5,12-o-benzenonaphthacene were suspended in 150 ml of CH$_3$CN at room temperature in a 250 ml three-necked flask. A solution of 0.73 g (2.6 mmol) of silver tosylate in 20 ml of CH$_3$CN was added dropwise to this mixture. The suspension was [lacuna] at 70° C. for two hours and then allowed to cool, the yellowish silver bromide was separated off, and the acetonitrile was evaporated in a rotary evaporator, leaving a relatively viscous substance, which was crystallized by addition of 3 ml of ether, filtered off with suction, rinsed with a little diethyl ether and dried, giving 1.0 g (80%) of crystalline 6-cyano-11-tosylmethyl-5,12-dihydro-5,12-o-benzenonaphthacene.

$^1$H-NMR; 400 MHz/CDCl$_3$: δ/ppm=2.28, (s, 3H), 5.96, (s, 2H), 6.02 and 6.03, (each s, each 1H), 6.73–6.75 (m, 2H), 7.13–7.20 (m, 6H), 7.52–7.61 (m, 6H), 7.89–7.91 (m, 1H), 8.01–8.03 (m, 1H).

EXAMPLE 22

Synthesis of 6-Cyano-11-formyl-5,12-dihydro-5,12-o-benzenonaphthacene

The crude product obtained from the reaction in EXAMPLE 21 was subsequently heated, without further purification, to 100° C. (5 minutes) together with 2 g of NaHCO$_3$ in 20 ml of abs. DMSO. After this time, the reaction was complete and was terminated by pouring the reaction mixture into 200 ml of water. The aldehyde which precipitated during this operation was filtered off with suction and dried, giving 0.7 g (65%) of virtually colorless 6-cyano-11-formyl-5,12-dihydro-5,12-o-benzenonaphthacene.

$^1$H-NMR; 400 MHz/DMSO: δ/ppm=6.16 and 6.89, (each s, each 1H), 7.14–7.15 (m, 4H), 7.63–7.68 (m, 4H), 7.74–7.78 (m, 2H), 8.06–8.08 (m, 1 H), 8.80–8.82 (m, 1H), 11.25 (s, 1H);

IR: v/cm$^{-1}$: 3069, 3024, 2915, 2222, 1690, 1462, 1195, 1158, 1048, 762, 599.

EXAMPLE 23

Synthesis of 6-Cyano-11-carboxyl-5,12-dihydro-5,12-o-benzenonaphthacene

A solution of 130 mg of sodium chlorite in 20 ml of water was added dropwise at room temperature to a suspension of 1.0 g (2.8 mmol) of 6-cyano-11-formyl-5,12-dihydro-5,12-o-benzenonaphthacene, 5 ml of $H_2O_2$, 15 ml of aqueous buffer solution and 100 ml of acetonitrile. A yellowish suspension is formed whose yellow coloration disappears during the reaction. The suspension was stirred at room temperature for four hours, ultimately resulting in a yellow solution.

30 ml of water were added, and the acetonitrile was evaporated in a rotary evaporator, causing the acid to crystallize out. The carboxylic acid was filtered off with suction and dissolved, while still moist, in 100 ml of 2N NaOH. The cloudy suspension was filtered through a fluted filter, and the clear, basic solution was acidified using conc. HCl, whereupon the acid precipitates out with a pale yellow coloration.

The acid was filtered off with suction and re-dissolved in dilute 2N sodium hydroxide solution. The basic solution was extracted once with a mixture of 30 ml of ether [lacuna] and separated off from the organic phase, and conc. HCl was added with vigorous stirring until a pH of 3 remained. Cooling and filtering off with suction gave 700 mg (68%) of 6-cyano-11-carboxyl-5,12-dihydro-5,12-o-benzenonaphthacene of melting point 346–350° C.

$^1$H-NMR; 400 MHz/DMSO: δ/ppm=5.93 and 6.13, (each s, each 1H), 7.11–7.16 (m, 4H), 7.54–7.56 (m, 2H), 7.66–7.77 (m, 4H), 7.95–7.97 (m, 1H) 8.05–8.07 (m, 1H), 14.4 (s, 1H); IR(KBr): ν/cm$^{-1}$: 3400–2700, 2222, 1735, 1693, 1510, 1461, 1196, 763, 747.

EXAMPLE 24

Synthesis of 2,5-bis((11'-Cyano-5',12'-dihydro-5', 12'-dihydro-5',12'-o-benzenonaphthacen)-6'-yl)-1,3, 4-oxadiazole 4.7 g (12.6 mmol) of 6-cyano-11-carboxyl-5,12-dihydro-5,12-o-benzenonaphthacene were suspended in 3 ml of abs. dimethylformamide in a 250 ml two-necked flask with exclusion of moisture, and 60 ml of freshly distilled thionyl chloride were added. The evolution of $SO_2$ and HCl which commenced immediately had substantially subsided after 15 minutes, and the solution was refluxed for 4 hours. DMF and excess thionyl chloride were subsequently distilled off under reduced pressure, and the residue was again stirred up with 50 ml of petroleum ether (90° C.) and again distilled off quickly (reduced pressure). A further 50 ml of petroleum ether were added, and the acid chloride was filtered off with suction under $N_2$ by means of a Schlenk apparatus and only dried a little, giving 7.4 g (150%) of virtually colorless, still-moist carboxylic acid chloride.

Half of the virtually colorless acid chloride obtained was dissolved in 100 ml of abs. dioxane and slowly added dropwise at room temperature to a solution of 2.0 ml of hydrazine hydrate (80%) in 25 ml of dioxane. When the addition was complete, the mixture was stirred for a further 1 hour. The reaction mixture was subsequently poured into 500 ml of water, and the precipitated product was filtered off with suction and dried, giving 2.02 g (82%) of colorless carbohydrazide, which was reacted further without purification.

The carbohydrazide was dissolved in a mixture of 50 ml of abs. $NEt_3$ and 50 ml of dioxane with exclusion of moisture and added dropwise at room temperature with vigorous stirring to a solution of the retained second half of the acid chloride in 120 ml of abs. dioxane. When the addition was complete, the mixture was refluxed for 2 hours, during which the solution increasingly became a darker color. The still-warm solution was poured into 200 ml of water and stirred briefly. The resultant precipitate was filtered off with suction, rinsed with plenty of water and dried, giving slightly brownish diaroylhydrazine, which was likewise reacted further without further purification.

4.5 g of the crude N,N'-dinaphthoyltriptycenehydrazine were refluxed for eight hours in 200 ml of freshly distilled phosphorus oxychloride. About 150 ml of $POCl_3$ were then distilled off, and the remaining solution was added dropwise to 300 ml of 2N NaOH. The pH was adjusted to 6–7 using 2N HCl. The resultant precipitate was filtered off with suction and dried (3.7 g=88%).

The crude product was dissolved in 350 ml of DME, refluxed for 30 minutes with activated carbon and then filtered through a fluted filter.

The remaining solution was evaporated to dryness in a rotary evaporator. The whitish beige solid was taken up in NMP and crystallized at 70° C. using MeOH. A further two crystallizations from dioxane/MeOH gave 450 mg of colorless 2,5-bis((11'-cyano-5',12'-dihydro-5',12'-o-benzenonaphthacen)-6'-yl)-1,3,4-oxadiazole, which could not be melted without decomposition. Tg=165° C.;

$^1$H NMR; 400 MHz/CDCl$_3$): δ/ppm=6.16 and 6.20 (2×s, each 2H), 7.08–7.17 (m, 8H), 7.43–7.44 (m, 4H), 7.71–7.63 (m, 4+2H) 7.69–7.73 (m, 2H), 8.09–8.11 (m, 2H), 8.226–8.28 (m, 2H); Mass: FD, m/e(%): 701.9 (100%), [M$^+$]; UV-VIS: Absorption: $\lambda_{max}$=340 nm; Fluorescence (solution): (solution 8E-6 mol/l), 411 nm (ε=45000); Fluorescence (film): spin coating, chlorobenzene, 10 mg/ml, 1000 rpm: 428 nm; IR(KBr): ν/cm$^{-1}$: 3069, 2959, 2850, 2223, 1550, 1506, 1460, 1156, 1121, 756, 577; Cyclic voltammetry: Reduction; 0.1M TBAHFP/THF, (Fc/Fc$^+$), 100 mV/s: $E^1_{1/2}$=–1.939 mV, $E^2_{1/2}$=–2108 mV.

Synthesis of (t-BuPD)$_2$NTrp

EXAMPLE 25

Synthesis of 6,11-Diformyl-5,12-dihydro-5,12-o-benzenonaphthacene 5.9 g (23 mmol) of silver p-toluenesulfonate in 50 ml of acetonitrile were added dropwise to a suspension of 4.70 g (10.6 mmol) of 6-bromomethyl-11-chloromethyl-5,12-dihydro-5,12-o-benzenonaphthacene in 300 ml of acetonitrile in a 500 ml two-necked flask, and the mixture was stirred overnight at room temperature with exclusion of light. The precipitated silver bromide was then separated off, and the acetonitrile was evaporated in a rotary evaporator. 10 ml of $Et_2O$ were added to the final 10 ml of solution, whereupon crystallization of the bistosylate commences. After cooling, the crystals were filtered off with suction, giving 4.2 9 (70%) of colorless 6,11-bis(tosylmethyl)-5,12-dihydro-5,12-o-benzenonaphthacene, which was suspended in 70 ml of dry DMSO and heated to 100° C. over the course of 15 minutes together with 5 g of $NaHCO_3$. The mixture was subsequently cooled, and the still-warm solution at about 50° C. was poured into 300 ml of water. The resultant precipitate was filtered off with suction and dried, giving 2.1 g (70%) of yellowish-beige crude product. Recrystallization from 80% strength acetic acid gave 1.7 g (65%) of yellowish crystalline 6,11-diformyl-5,12-dihydro-5,12-o-benzenonaphthacene of melting point 272–277° C.

$^1$H-NMR: (400 MHz/CDCl$_3$): δ/ppm=2.39 (s, 6H), 5.26 (s, 4H), 5.66 (s, 2H), 6.69 (s, 2H), 6.98–7.00 (m, 4H), 7.17–7.19 (m, 4H), 7.33–7.35 (m, 4H), 7.65–7.67 (m, 4H); IR(KBr): ν/cm$^{-1}$: 3069, 3020, 2870, 1685,1462,1213, 1160, 981, 753,633, 553.

EXAMPLE 26

Synthesis of 5,12-Dihydro-5,12-o-benzenonaphthacene6,11-dicarboxylic Acid 2.41 g (6.7 mmol) of 6,11-diformyl-5,12-dihydro-5,12-o-benzenonaphthacene were suspended in a mixture of 200 ml of acetonitrile, 10 ml of 30% strength hydrogen peroxide and 20 ml of buffer solution (pH 3) at room temperature in a 1 l two-necked flask. 1.70 g (19 mmol) of sodium chlorite (80%) in 10 ml of water were added dropwise via a dropping funnel. After a reaction time of two hours, a further 30 ml of water were added to the resultant yellowish solution, and the acetonitrile was removed in a rotary evaporator. The precipitate which formed was filtered off with suction after cooling and rinsed with a little water.

The still-moist acid was dissolved in 100 ml of 3N NaOH and extracted once with 30 ml of diethyl ether. After the basic solution had been cooled in an ice bath, conc. HCl was added to pH 3 in order to completely precipitate the acid. The precipitate was filtered off with suction and carefully dried, giving 2.5 g (96%) of colorless crystalline 5,12-dihydro-5,12-o-benzenonaphthacene-6,11-dicarboxylic acid of melting point 318–323° C.

$^1$H NMR; (400 MHz/DMSO): δ=5.88 (s, 2H), 7.08–7.11 (m, 4H), 7.48–7.50 (m, 4H), 7.57–7.60 (m, 2H), 7.88–7.91 (m, 2H), 13.96 (s, 2H); IR: v/cm$^{-1}$: 3424, 3400–2650, 2641, 1695, 1460, 1242, 1208, 766, 566.

EXAMPLE 27

Synthesis of 5,12-Dihydro-5,12-o-benzenonaphthacene6,11-dicarbonyl dichloride 2.4 g (6 mmol) of 5,12-dihydro-5,12-o-benzenonaphthacene-6,11-dicarboxylic acid were suspended in 1.5 ml of abs. DMF in a 100 ml round-bottomed flask with exclusion of moisture, and 50 ml of thionyl chloride were subsequently added at room temperature. The evolution of gas which immediately commenced had substantially subsided after 15 minutes, after which the mixture was refluxed for eight hours. The thionyl chloride was then distilled off, and 3×30 ml of petroleum ether were added and re-distilled off. 50 [lacuna] of petroleum ether were then added, and the product was filtered off with suction with exclusion of moisture, giving 2.3 g (96%) of virtually colorless 5,12-dihydro-5,12-o-benzenonaphthacene-6,11-dicarbonyl dichloride.

EXAMPLE 28

Synthesis of 6,11-bis(5'-(p-tert-Butylphenyl)-1,3,4-oxadiazol)-2'-yl)-5,12-dihydro-5,12-o-benzenonaphthacene (tBuPD)$_2$NTrp 1.0 g (2.55 mmol) of 5,12-dihydro-5,12-o-benzenonaphthacene-6,11-dicarboxylic acid were suspended in 2 ml of abs. dimethylformamide at room temperature in a 200 ml two-necked flask with exclusion of moisture, and 10 ml of freshly distilled thionyl chloride were added. The evolution of SO$_2$ and HCl which commenced immediately had substantially subsided after 15 minutes, after which the solution was refluxed for 3 hours. DMF and excess thionyl chloride were distilled off under reduced pressure, and the residue was stirred up a further three times with 30 ml of petroleum ether (b.p. 90° C.) each time and the solvent was re-distilled off. The yellowish acid chloride obtained was filtered off with suction with exclusion of moisture and then dissolved in 30 ml of abs. pyridine, a solution of 1.1 g (5.30 mmol) of p-tert-butylphenyltetrazole in 20 ml of pyridine was added, and the mixture was subsequently refluxed for 2 hours. The cooled solution was poured into 300 ml of water, and the resultant precipitate was filtered off with suction and dried. The resultant crude product was dissolved in chloroform and extracted twice with 100 ml of 2N HCl each time and washed with 100 ml of water. The organic phase was dried over Na$_2$SO$_4$ and evaporated in a rotary evaporator. Chromatography using hexane/EE 1:1 over silica gel gave 600 mg of colorless, strongly blue-fluorescent 6,11-bis(5-(p-tert-butylphenyl-1,3,4-oxadiazol)-2'-yl)-5,12-dihydro-5,12-o-benzenonaphthacene of melting point 285° C.–288° C. (T$_g$=165° C.). $^1$H-NMR; 400 MHz/DMSO: δ=1.38 (s, 18H) 6.15 (s, 2H), 7.13–7.15 (m, 4H), 7.55–7.58 (m, 4H), 7.63–7.65 (m, 2H), 7.75–7.78 (m, 4H), 8.04–8.06 (m, 2H), 8.15–8.18 (m, 4H); IR(KBr): vv/cm$^{-1}$: 3070–3050, 2960–2868, 1614, 1548, 1495, 1192, 1188, 842, 763; Mass: FD, 8 kV: m/e: 704.1 (100%) [M$^+$]; UV-VIS: Absorption: λ$_{max}$=318 nm (ε=50000); Fluorescence (solution): (CH$_2$Cl$_2$: 10$^{-6}$ mol/l), 433 nm; Fluorescence (film): spin coating, chlorobenzene, [1000 rpm], 10 mg/ml, λ$_{Em}$=423 nm; Cyclic voltammetry: Reduction; 0.1M TBAHFP/THF, (Fc/Fc$^+$), 100 mV/s: E$^1_{1/2}$=–2140 mV, E$^2_{1/2}$=–2333 mV (irrev.).

What is claimed is:

1. An electroluminescent device comprising an electroluminescent material, said electroluminescent material comprising a triptycene derivative of the formula (I),

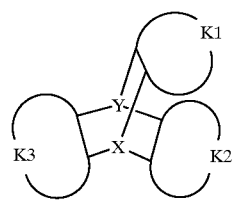

(I)

where the symbols in the formula have the following meanings:

K$^1$, K$^2$, and K$^3$ are identical or different and are mono- or polycyclic systems, which optionally contain heteroatoms and are substituted or unsubstituted;

X and Y are identical or different and are CR$^1$, N, P, As, or SIR$^2$;

R$^1$ are identical or different and are H, halogen, pseudohalogen or a hydrocarbon radical having 1 to 30 carbon atoms which optionally contain heteroatoms;

R$^2$ are identical or different and are a hydrocarbon radical having 1 to 30 carbon atoms which optionally contain heteroatoms.

2. The device of claim 1, wherein at least one of the group comprising K$^1$, K$^2$, and K$^3$ in the formula (I) is a fluorophore.

3. The device of claim 1, wherein the groups K$^{1-3}$ are conjugated systems.

4. The device of claim 1, wherein the triptycene derivative is a compound of the formula (II) or of the formula (III),

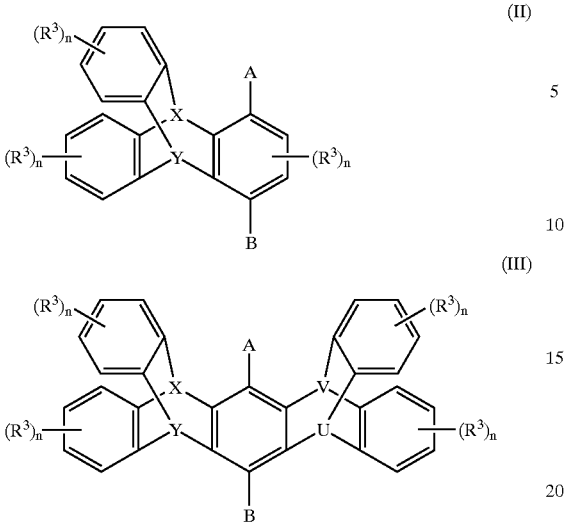

where the symbols and indices have the following meanings:
X, Y, U, and V are identical or different and are $CR^1$, N, P, As or $SiR^2$;
$R^1$ are identical or different and are H, halogen, pseudohalogen or a hydrocarbon radical having 1 to 30 carbon atoms which optionally contain heteroatoms;
$R^2$ are identical or different and are a hydrocarbon radical having 1 to 30 carbon atoms which optionally contain heteroatoms;
$R^3$ are identical or different and are F, Cl, Br, I, CN, $NO_2$, a branched or unbranched alkyl group having 1 to 22 carbon atoms, where one or more —$CH_2$— groups may be replaced by —O—, —S—, —$SO_3$—, —O—CO—, —CO—O—, aryl or heteroaryl (in each case having 4 to 10 carbon atoms), with the proviso that two oxygen atoms cannot be bonded directly to one another, and where one, more or all H atoms may be replaced by F, and where two substituents $R^3$ on the same ring may be linked to one another to form a ring or a further fused ring system or may also be hydrogenated, optionally partially hydrogenated, and may carry substituents, with the proviso that the number of substituents is not greater than the total number of carbon atoms of $R^3$;
n are identical or different are 0, 1, 2, 3, 4 or 5;
A and B are identical or different and are groups of the formula

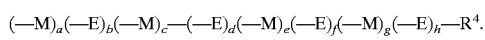

where the symbols and indices have the following meanings:
M are identical or different and are —$CR^5$=$CR^6$—, —C≡C—, —$CR^7$=N— or —N=$CR^7$—;
E are identical or different and are pyrazine-2,5-diyl, pyridazine-3,6-diyl, pyradine-2,5-diyl, pyrimidine-2,5-diyl, 1,3,4-thiadiazole-2,5-diyl, 1,3-thiazole-2,4-diyl, 1,3-thiazole-2,5-diyl, thiophene-2,4-diyl, thiophene-2,5-diyl, naphthalene-2,6-diyl, naphthalene-1,4-diyl or naphthalene-1,5-diyl, in which one or two CH groups may be replaced by N, 1,3-oxazole-2,4-diyl, 1,3-oxazole-2,5-diyl, 1,3,4-oxadiazole-2,5-diyl, 4,4'-biphenylene, anthracenediyl, carbazolediyl, benzoxazolediyl, indene-2,5-diyl or indene-2,6-diyl, where one or more H atoms in the ring systems may be substituted by radicals $R^8$,
$R^4$, $R^5$, $R^6$, and $R^7$ are identical or different and are
a) hydrogen, —F, —Cl, —$CF_3$, —CN, or $NR^9R^{10}$,
b) a straight-chain or branched alkyl radical (with or without an asymmetrical carbon atom) having 1 to 20 carbon atoms, where
b1) one or more non-adjacent and non-terminal $CH_2$ groups may be replaced by —O—, —S—, —CO—, —CO—O—, —O—CO—, —O—CO—O— or —$Si(CH_3)_2$—, and/or
b2) one or more $CH_2$ groups may be replaced by —CH=CH—, —C≡C—, cyclopropane-1,2-diyl, 1,4-phenylene, 1,4-cyclohexylene or 1,3-cyclopentylene, and/or
b3) one or more H atoms may be replaced by F, CN and/or Cl; are identical or different and are
a) —F, —Cl, —$CF_3$, —CN o r $NO_2$
b) a straight-chain or branched alkyl radical (with or without an asymmetrical carbon atom) having 1 to 20 carbon atoms, where
b1) one or more non-adjacent and non-terminal $CH_2$ groups may be replaced by —O—, —S—, —CO—, —CO—O—, —O—CO—, —O—CO—O— or —NH—, $N(C_1$-$C_{10}$-alkyl), —N-phenyl-, —N-tolyl, —$N(C_2H_5$—$OCH_3)$— or —$Si(CH_3)_2$—, and/or
b2) one or more $CH_2$ groups may be replaced by —CH=CH—, —C≡C—, 1,4-phenylene, and/or
b3) one or more H atoms may be replaced by F, CN and/or Cl;
$R^9$ and $R^{10}$ are identical or different and are
a) hydrogen,
b) a straight-chain or branched alkyl radical (with or without an asymmetrical carbon atom) having 1 to 20 carbon atoms, where
b1) one or more $CH_2$ groups which are not adjacent to one another or to the nitrogen may be replaced by —O—, —S—, —CO—, —CO—O—, —O—CO—, —O—CO— or —$Si(CH_3)_2$-, and/or
b2) one or more $CH_2$ groups may be replaced by —CH=CH—, —C≡C—, cyclopropane-1,2-diyl, 1,4-phenylene, 1,4-cyclohexylene or 1,3-cyclopentylene, and/or
b3) one or more H atoms may be replaced by F, CN and/or Cl and
b4) $R^8$ and $R^9$ together may also form a ring;
a, b, c, d, e, f, g and h, independently of one another, are 0 or 1.
5. The device of claim 4, wherein the sum of the indices a-h in the formula (II) or (III) is at least 1.
6. The device of claim 5, wherein the triptycene derivative is of the formula (IV), (V) or (VI)

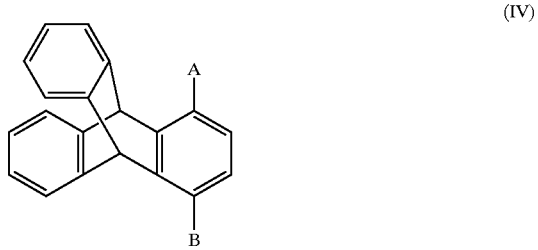

(V)
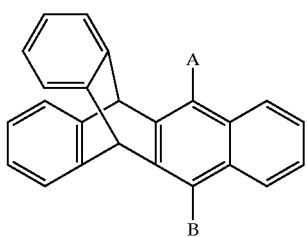
(VI)
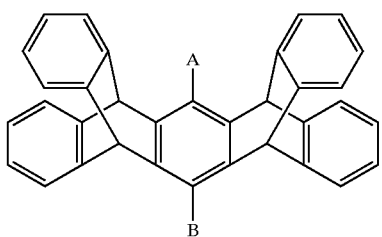
where the groups A and B are as defined in the formulae (II) or (III).
7. The device of claim 6, wherein the triptycene derivative is selected from the group comprising (IVa-i), (Va-i), and (VIa-i):
(IVa)
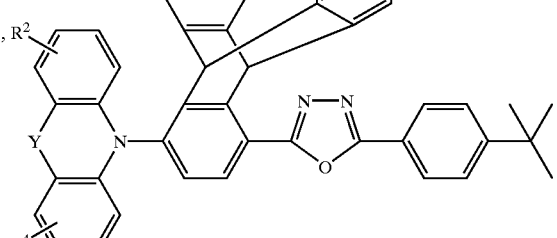
(Va)
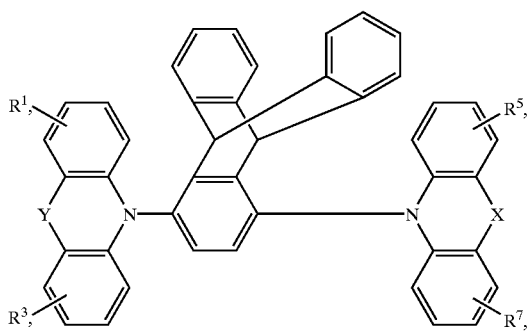
(VIa)
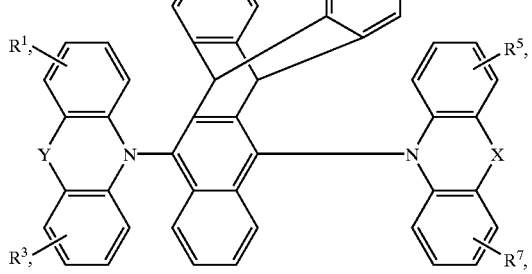
(IVb)
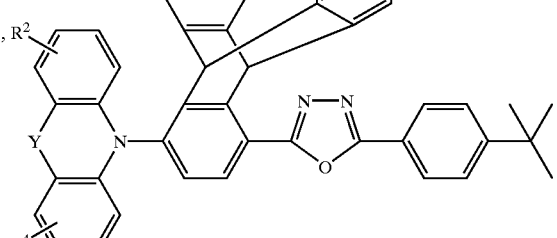
(IVc)
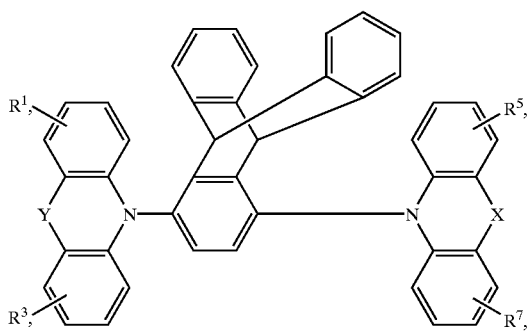
(Vb)
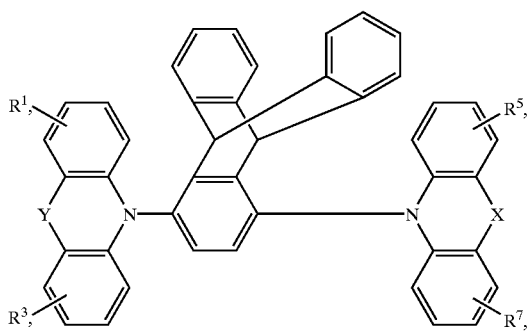
(Vc)
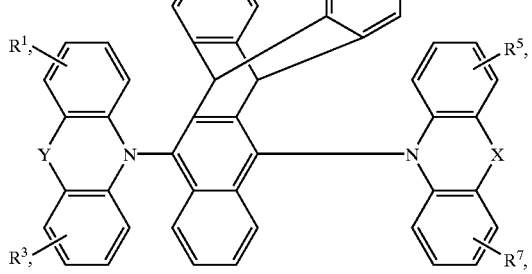

(VIb)
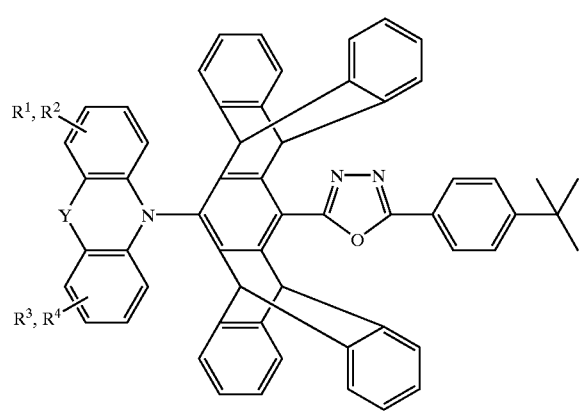
(VId)
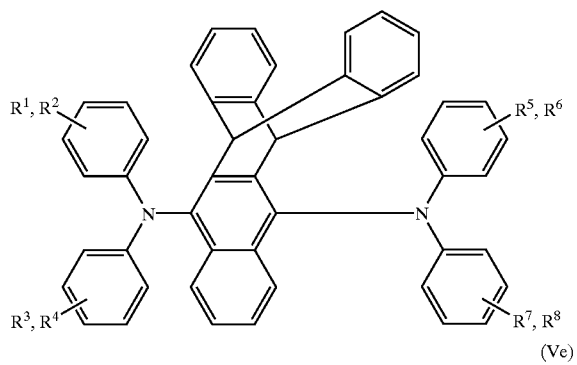
(VIc)
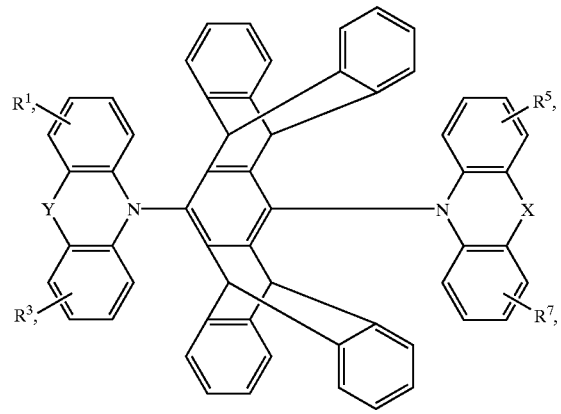
(Ve)
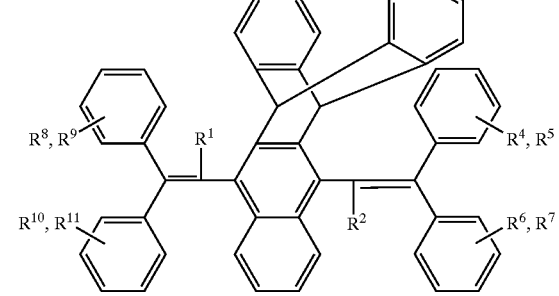
(IVd)
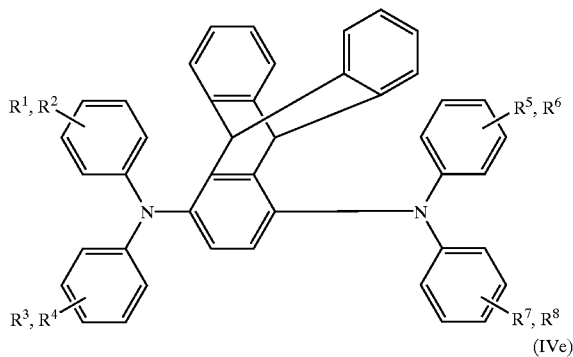
(VId)
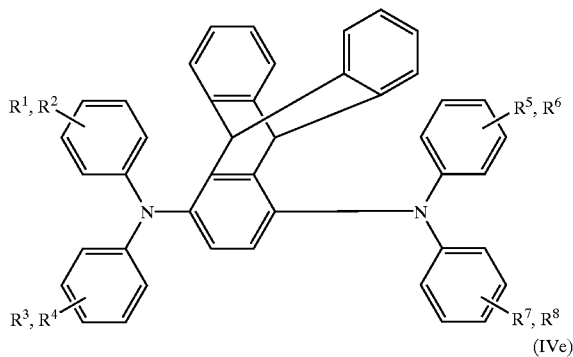
(IVe)
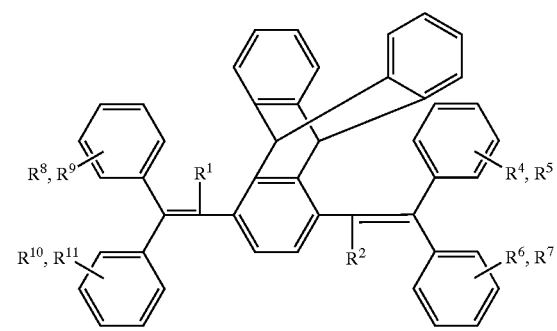
(VIe)
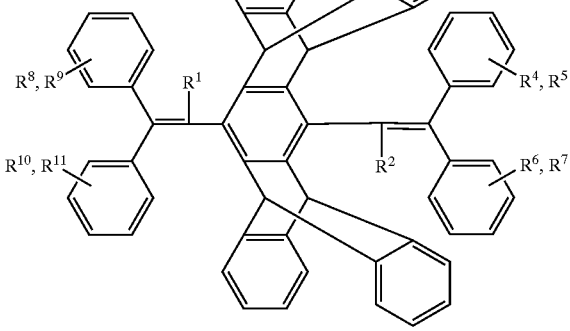

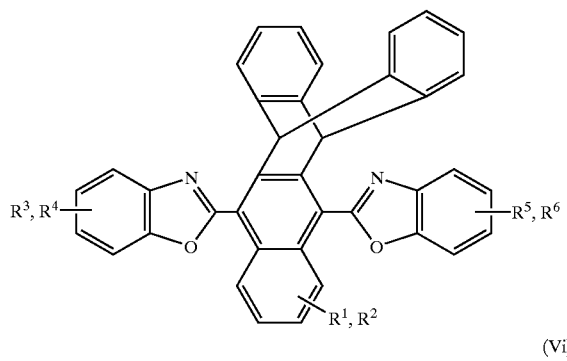

(Vh)

(Vi)

(VIh)

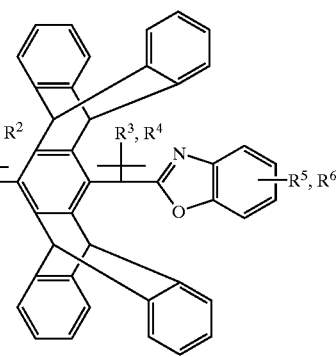

(VIi)

where the symbols have the following meanings:

y is —O—, —S—, —NR$^{11}$— or —CR$^{10}$R$^{11}$—;

R$^{1-11}$ are identical or different and are F, Cl, Br, I, CN, NO$_2$, a branched or unbranched alkyl group having 1 to 22 carbon atoms, where one or more —CH$_2$— groups may be replaced by —O—, —S—, —SO$_3$—, —O—CO—, —CO—O—, aryl or heteroaryl (in each case having 4 to 10 carbon atoms), with the proviso that two oxygen atoms cannot be bonded directly to one another, and where one, more or all H atoms may be replaced by F, and where two substituents R$^{1-11}$ on the same ring may be linked to one another to form a ring or a further fused ring system or may also be hydrogenated, optionally partially hydrogenated, and may carry substituents, with the proviso that the number of substituents is not greater than the total number of carbon atoms on R$^{1-11}$.

8. An electroluminescent device comprising one or ore active layers, wherein at least one active later contains at least one triptycene derivative of claim 1.

* * * * *

UNITED STATES PATENT AND TRADEMARK OFFICE
CERTIFICATE OF CORRECTION

PATENT NO.    : 6,509,110 B1
DATED         : January 21, 2003
INVENTOR(S)   : Josef Salbeck et al.

It is certified that error appears in the above-identified patent and that said Letters Patent is hereby corrected as shown below:

Title page,
Item [54], Title, please delete "ELECTRONICS" and insert
-- ELECTRONIC --.

Column 32,
Line 42, before "or" please delete "-O-CO-" and insert -- O-CO-O --.

Signed and Sealed this

Eighteenth Day of March, 2003

JAMES E. ROGAN
*Director of the United States Patent and Trademark Office*